United States Patent
Wakita et al.

(10) Patent No.: US 12,133,910 B2
(45) Date of Patent: Nov. 5, 2024

(54) OIL AGENT-CONTAINING SILICONE ELASTOMER PARTICLE AND USE THEREOF IN COSMETIC COMPOSITION, ETC

(71) Applicant: DOW TORAY CO., LTD., Tokyo (JP)

(72) Inventors: Mari Wakita, Ichihara (JP); Hiroko Taniguchi, Ichihara (JP); Yasue Kanzaki, Ichihara (JP); Seiji Hori, Ichihara (JP)

(73) Assignee: DOW TORAY CO., LTD., Tokyo (JP)

( * ) Notice: Subject to any disclaimer, the term of this patent is extended or adjusted under 35 U.S.C. 154(b) by 186 days.

(21) Appl. No.: 17/041,699

(22) PCT Filed: Mar. 27, 2019

(86) PCT No.: PCT/JP2019/013253
§ 371 (c)(1),
(2) Date: Sep. 25, 2020

(87) PCT Pub. No.: WO2019/189394
PCT Pub. Date: Oct. 3, 2019

(65) Prior Publication Data
US 2021/0113452 A1    Apr. 22, 2021

(30) Foreign Application Priority Data

Mar. 27, 2018   (JP) .................. 2018-059333

(51) Int. Cl.
| | |
|---|---|
| *A61K 8/891* | (2006.01) |
| *A61K 8/02* | (2006.01) |
| *A61K 8/06* | (2006.01) |
| *A61K 8/19* | (2006.01) |
| *A61K 8/23* | (2006.01) |
| *A61K 8/25* | (2006.01) |

(Continued)

(52) U.S. Cl.
CPC ............ *A61K 8/891* (2013.01); *A61K 8/0208* (2013.01); *A61K 8/022* (2013.01); *A61K 8/0241* (2013.01); *A61K 8/062* (2013.01); *A61K 8/064* (2013.01); *A61K 8/19* (2013.01); *A61K 8/23* (2013.01); *A61K 8/25* (2013.01); *A61K 8/26* (2013.01); *A61K 8/27* (2013.01); *A61K 8/29* (2013.01); *A61K 8/31* (2013.01); *A61K 8/345* (2013.01); *A61K 8/365* (2013.01); *A61K 8/368* (2013.01); *A61K 8/37* (2013.01); *A61K 8/41* (2013.01); *A61K 8/416* (2013.01); *A61K 8/4946* (2013.01); *A61K 8/585* (2013.01); *A61K 8/60* (2013.01); *A61K 8/735* (2013.01); *A61K 8/8117* (2013.01); *A61K 8/8147* (2013.01); *A61K 8/8158* (2013.01); *A61K 8/86* (2013.01); *A61K 8/894* (2013.01); *A61K 8/92* (2013.01); *A61K 8/922* (2013.01); *A61K 8/925* (2013.01); *A61Q 1/02* (2013.01); *A61Q 1/04* (2013.01); *A61Q 1/08* (2013.01); *A61Q 1/10* (2013.01); *A61Q 1/12* (2013.01); *A61Q 5/065* (2013.01); *A61Q 17/04* (2013.01); *A61Q 19/00* (2013.01); *A61Q 19/007* (2013.01); *A61Q 19/08* (2013.01); *A61K 2800/10* (2013.01); *A61K 2800/412* (2013.01)

(58) Field of Classification Search
CPC ...... A61K 8/891; A61K 8/0208; A61K 8/022; A61K 8/0241; A61K 8/062; A61K 8/064; A61K 8/19; A61K 8/23; A61K 8/25; A61K 8/26; A61K 8/27; A61K 8/29; A61K 8/31; A61K 8/345; A61K 8/365; A61K 8/368; A61K 8/37; A61K 8/41; A61K 8/416; A61K 8/4946; A61K 8/585; A61K 8/60; A61K 8/735; A61K 8/8117; A61K 8/8147; A61K 8/8158; A61K 8/86; A61K 8/894; A61K 8/92; A61K 8/922; A61K 8/925; A61K 2800/10; A61K 2800/412; A61Q 1/02; A61Q 1/04; A61Q 1/08; A61Q 1/10; A61Q 1/12; A61Q 5/065; A61Q 17/04; A61Q 19/00; A61Q 19/007; A61Q 19/08
See application file for complete search history.

(56) References Cited

U.S. PATENT DOCUMENTS

| | | |
|---|---|---|
| 4,980,167 A | 12/1990 | Harashima et al. |
| 6,419,912 B1 | 7/2002 | Lezer |

(Continued)

FOREIGN PATENT DOCUMENTS

| | | |
|---|---|---|
| CN | 101395206 A | 3/2009 |
| CN | 104844945 A | 8/2015 |

(Continued)

OTHER PUBLICATIONS

Dow Corning Toray, machine translation of JP 2009530477 via FIT, 2009 (Year: 2009).*

(Continued)

*Primary Examiner* — Bethany P Barham
*Assistant Examiner* — Ayaan A Alam
(74) *Attorney, Agent, or Firm* — WARNER NORCROSS + JUDD LLP

(57) ABSTRACT

Provided is an oil-including elastomer particle wherein at least two silicon atoms within the silicone elastomer particle are cross-linked through a silalkylene group with a carbon number of between 4 and 20, and having a structure that includes, in the silicone elastomer particle, an oil that is liquid at 40° C. In general, the mixture of oil and the cross-linking silicone composition can be cured in the form of emulsion particles. Also provided herein are uses of the oil-including elastomer particle and emulsion particles formed therefrom.

20 Claims, No Drawings

(51) Int. Cl.

| | | |
|---|---|---|
| *A61K 8/26* | (2006.01) | |
| *A61K 8/27* | (2006.01) | |
| *A61K 8/29* | (2006.01) | |
| *A61K 8/31* | (2006.01) | |
| *A61K 8/34* | (2006.01) | |
| *A61K 8/365* | (2006.01) | |
| *A61K 8/368* | (2006.01) | |
| *A61K 8/37* | (2006.01) | |
| *A61K 8/41* | (2006.01) | |
| *A61K 8/49* | (2006.01) | |
| *A61K 8/58* | (2006.01) | |
| *A61K 8/60* | (2006.01) | |
| *A61K 8/73* | (2006.01) | |
| *A61K 8/81* | (2006.01) | |
| *A61K 8/86* | (2006.01) | |
| *A61K 8/894* | (2006.01) | |
| *A61K 8/92* | (2006.01) | |
| *A61Q 1/02* | (2006.01) | |
| *A61Q 1/04* | (2006.01) | |
| *A61Q 1/08* | (2006.01) | |
| *A61Q 1/10* | (2006.01) | |
| *A61Q 1/12* | (2006.01) | |
| *A61Q 5/06* | (2006.01) | |
| *A61Q 17/04* | (2006.01) | |
| *A61Q 19/00* | (2006.01) | |
| *A61Q 19/08* | (2006.01) | |

(56) References Cited

U.S. PATENT DOCUMENTS

| | | |
|---|---|---|
| 2002/0016382 A1 | 2/2002 | Kondo et al. |
| 2006/0104929 A1 | 5/2006 | Morita et al. |
| 2010/0172849 A1 | 7/2010 | Shaow et al. |
| 2014/0335044 A1 | 11/2014 | Inokuchi et al. |
| 2015/0306019 A1 | 10/2015 | Wakita |
| 2018/0215877 A1* | 8/2018 | Hori .............. A61K 8/0241 |
| 2020/0332124 A1 | 10/2020 | Wakita et al. |

FOREIGN PATENT DOCUMENTS

| | | | |
|---|---|---|---|
| EP | 1731136 A1 * | 12/2006 | ............ A61K 8/02 |
| EP | 1536765 B1 | 10/2007 | |
| EP | 3453736 A1 | 3/2019 | |
| EP | 3904427 A1 | 11/2021 | |
| JP | H02243612 A | 9/1990 | |
| JP | H07316014 A | 12/1995 | |
| JP | 2004124083 A | 4/2004 | |
| JP | 2009530477 A | 8/2009 | |
| JP | 20100095466 A | 4/2010 | |
| WO | 2017191798 A1 | 11/2017 | |
| WO | 2019124418 A1 | 6/2019 | |

OTHER PUBLICATIONS

Wakita, 2017, Machine Translation of WO 201791798 A1 via PE2E FIT (Year: 2017).*

Kani, et al., Machine translation of EP-1731136-A1 from PE2E via FIT, 2006 (Year: 2006).*

English translation of International Search Report for PCT/JP2019/013253 dated Jun. 25, 2019, 2 pages.

Machine assisted English translation of JPH07316014A obtained from https://patents.google.com/patent on Sep. 25, 2020, 7 pages.

Machine assisted English translation of CN104844945A obtained from https://patents.google.com/patent on Dec. 14, 2021, 8 pages.

Machine assisted English translation of CN101395206A obtained from https://patents.google.com/patent on Dec. 14, 2021, 25 pages.

Machine assisted English translation of JP20100095466A obtained from https://patents.google.com/patent on Dec. 14, 2021, 18 pages.

* cited by examiner

OIL AGENT-CONTAINING SILICONE ELASTOMER PARTICLE AND USE THEREOF IN COSMETIC COMPOSITION, ETC

CROSS-REFERENCE TO RELATED APPLICATIONS

This application is the National Stage of International Appl. No. PCT/JP2019/013253 filed on 27 Mar. 2019, which claims priority to and all advantages of Japanese Appl. No. 2018-059333 filed on 27 Mar. 2018, the content of which is hereby incorporated by reference.

FIELD OF TECHNOLOGY

The present invention relates to an oil-including silicone elastomer particle which, when compared to a conventional product, has low oil absorption and is resistant to cohesion, and thus has superior ease of handling as a raw material for cosmetics, and can apply a superior texture and feeling in use to cosmetics. Moreover, the present invention relates to a cosmetic material that includes oil-including silicone elastomer particles, to a cosmetic composition, to an organic resin additive, and to other applications thereof, and to a method for manufacturing the oil-including silicone elastomer particle.

PRIOR ART

Silicone elastomer particles are made through curing addition reaction-curable silicone compositions or condensation reaction-curable silicone compositions, and the particle diameters and oil absorptions thereof differ depending on the method for manufacturing. In general, a method for manufacturing that produces silicone particles of a small particle diameter through causing a curing reaction of a particle form of a cross-linkable silicone composition is preferred given that there is a limit to the fineness produced when producing grains through pulverizing a hardened material. However, even if the primary particles are fine, there is a tendency for agglomeration into secondary particles with the passage of time, where the agglomerated particles cannot be redispersed easily into primary particles. This is caused by a phenomenon wherein the combination as agglomerated particles is difficult to break down (separate) once primary particles have combined together.

When highly cohesive silicone particles are mixed in a solvent, or the like, the silicone particles do not disperse to the primary particle size, but rather form secondary agglomerated particles or agglomerations, making it impossible to prepare a uniform mixture with adequate dispersion. Because of this, compositions that include silicone particles have been unable to demonstrate fully the distinctive benefits of the silicone particles, and, in particular, as a cosmetic raw material or organic resin material, there have been issues with inadequate ease of handling, storage stability, and stability when mixed into a system. Note that typically there is a tendency for soft rubbery particles, such as silicone elastomer particles, to agglomerate with the passage of time.

Improvements in the feel in use and texture of cosmetics through addition, at the end, of liquid oil (oil for cosmetics) to silicone elastomer particles, when using silicone elastomer particles as a cosmetic raw material, to use the liquid oil and the silicone elastomer particles in combination, have been proposed broadly (for example, Patent Document 1). However, as described above there is a tendency for silicone elastomer particles to agglomerate with the passage of time, where this property has an effect on the absorption of oil by the silicone particles, so in some cases the improvement in feel in use and texture, anticipated for the cosmetics, may be inadequate.

On the other hand, the present applicant has proposed a silicone particle as a silicone particle that has superior dispersibility, high lipophilicity, and superior storage stability, wherein the per-unit-mass silicon atom-bound hydrogen atom inclusion proportion, described in Patent Document 2, is low, and includes alkylene groups with carbon numbers between 4 and 20, which cure a cross-linkable composition for forming silicone particles that include alkenyl groups with between 4 and 20 carbon atoms, such as hexenyl groups. However, while these silicone particles achieve an improvement in, for example, dispersion stability as a cosmetic raw material, when mixed into a cosmetic in combination with liquid oil, as described above, there is still room for improvement in terms of the texture and the feel-in-use thereof.

On the other hand, in Patent Document 3, and the like, the present applicant has proposed the ability to produce an oil-including silicone particle, along with the use thereof in a cosmetic application, wherein liquid oil is included in the silicone particle through emulsifying in water a cross-linkable silicone composition that includes a vinyl group as a cross-linkable functional group, together with a liquid oil, such as polydimethyl siloxane, to form cross-linkable silicone emulsion particles, which are then cured through a hydrosilylation reaction catalyst such as of platinum.

However, when compared to normal silicone elastomer particles, these publicly known oil-including silicone particles tend to have greater softness and tend to result in tackiness, and thus tend to agglomerate with the passage of time, and so if they are not redispersed through the use of mechanical force prior to mixing, they cannot be mixed with stability, and thus are inadequate in terms of ease of handling, storage stability, and stability when mixing into a system, as a cosmetic raw material or organic resin additive, and there is still room for improvement in terms of texture and feel in use when mixed into a cosmetic in combination with a liquid oil.

PRIOR ART DOCUMENTS

Patent Documents

[Patent Document 1] Japanese Unexamined Patent Application Publication H07-316014
[Patent Document 2] International Patent Application Publication WO 2017/191798
[Patent Document 3] Japanese Unexamined Patent Application Publication H02-243612

SUMMARY OF THE INVENTION

Problem Solved by the Present Invention

Moreover, the present inventors have discovered a new issue in silicone particles that include alkylene groups of carbon numbers between 4 and 20, proposed in Patent Document 2. While the silicone particles achieve an improvement in dispersion stability, and the like, and given their superior lipophilicity, even when mixed with oil there are few problems with dispersion failures, or the like, the result of the silicone particles as a whole having high lipophilicity and oil absorption, which causes the oil that is mixed into the cosmetic composition to be absorbed during mixing or storage, is that it is difficult to produce the texture or feel in use that is expected in a cosmetic after mixing, and the fluidity or viscosity and external appearance of the preparation may be compromised. Consequently, from the perspective of stability when mixing into a cosmetic and of ease of handling, there is the need to provide a silicone particle that can achieve lower oil absorption while maintaining cohesiveness and lipophilicity that is at least equal to the silicone particles proposed in Patent Document 2. However, adequate improvements cannot be produced through simply adding oil after the fact to the silicone particles proposed in Patent Document 2 to cause them to swell. Moreover, even given oil-including silicone particles that are publicly known, proposed in Patent Document 3, and the like, these cannot provide silicone particles that include also benefits such as described above.

Consequently, the object of the present invention is to provide a silicone elastomer particle, and a method for manufacturing thereof, that, when mixed into a cosmetic composition, or the like, has low oil absorption, is superior in improving the effects of softness and the texture and feel in use as a cosmetic, and which, when compared to a conventional silicone elastomer particle or oil-including silicone particle, suppresses agglomeration over time, and that is superior in ease of handling, storage stability, and stability when mixed into a system, as a cosmetic raw material, or the like. Moreover, an object of the present invention is to use a silicone elastomer particle to provide a cosmetic raw material and an organic resin additive that are superior in ease of handling, and the like, and in other applications. Moreover, an object of the present invention is to provide a cosmetic composition, which includes the silicone elastomer particles, with a feeling in use and storage stability.

Means for Solving the Problem

As the result of earnest research in order to solve the problems set forth above, the present inventors arrived at the present invention through the discovery that it is possible to solve the problems described above through the use of an oil-including silicone elastomer particle that has a structure wherein oil that is liquid at 40° C. is included in the silicone elastomer particle, with a structure wherein at least two silicon atoms within the silicone elastomer particle are cross-linked through a silalkylene group with a carbon number between 4 and 20. From the perspective of achieving low oil absorption it is particularly preferable that this oil-including silicone elastomer particle has a structure that includes, in the silicone elastomer particle, oil that is liquid at 40° C., derived from the cross-linkable silicone emulsion particle, through causing a cross-linking reaction of a silicone elastomer particle through causing a cross-linking reaction, in water, of a cross-linkable silicone emulsion particle that is produced through emulsification, in water, of a mixture of a cross-linkable silicone composition and oil that is a liquid at 40° C.

The present inventors arrived at the present invention through the discovery that it is possible to solve the problems set forth above through the use of an oil-including silicone elastomer, described above, as a cosmetic raw material and in other applications, and through a cosmetic raw material including the same.

That is, the object of the present invention is achieved through:

[1] An oil-including silicone elastomer particle that has a structure that includes, in the silicone elastomer particle, an oil that is a liquid at 40° C., having a structure wherein at least two silicon atoms within the silicone elastomer particle are cross-linked through a silalkylene group with a carbon number between 4 and 20.

Preferably, it may be:

[2] An oil-including silicone elastomer particle as set forth in [1] that is a silicone elastomer particle produced through a cross-linking reaction, in water, of a cross-linkable silicone emulsion particle produced through emulsification, in water, a mixture of a cross-linkable silicone composition that includes at least an organopolysiloxane wherein there are at least two alkenyl groups, with carbon numbers between 4 and 20, within the molecule, and an oil that is liquid at 40° C., having a structure wherein at least two silicon atoms within the silicone elastomer particle are cross-linked through a silalkylene group with a carbon number between 4 and 20, to include, in the silicone elastomer particle, an oil that is liquid at 40° C. that is derived from the cross-linkable silicone emulsion particle.

[3] An oil-including silicone elastomer particle as set forth in [1] or [2] wherein: the oil that is liquid at 40° C. is a non-reactive oil that does not have a reactive functional group within the molecule.

[4] An oil-including silicone elastomer particle as set forth in any one of [1] through [3], wherein: the oil that is liquid at 40° C. is one or more selections from silicone oils, hydrocarbon oils, and ester oils that have no reactive functional groups within the molecules.

[5] An oil-including silicone elastomer particle as set forth in any one of [1] through [4], wherein: the inclusion proportion of oil that is a liquid at 40° C. is in a range of between 5 and 60 mass % in respect to the particle as a whole.

[6] An oil-including silicone elastomer particle as set forth in any one of [1] through [5], wherein: the average particle diameter measured through a laser diffraction/scattering method is between 0.5 and 20 μm.

[7] An oil-including silicone elastomer particle as set forth in any one of [1] through [6], wherein: for the silicone elastomer particle in a state that does not include oil that is liquid at 40° C., the JIS-A hardness, measured through curing in the form of a sheet, in a state that does not include oil that is liquid at 40° C., the cross-linkable silicone composition that is used to form the silicone elastomer particle, is in a range between 10 and 80.

[8] An oil-including silicone elastomer particle as set forth in any one of [1] through [7], wherein: the silalkylene groups included in the silicone elastomer particles are substantially only silalkylene groups with carbon numbers of between 4 and 8, where the inclusion proportion of silalkylene groups with carbon numbers of 3 and below is less than 5 mass % in respect to the silicone elastomer particle.

[9] An oil-including silicone elastomer particle as set forth in any one of [1] through [8], wherein: the inclusion proportion of silicon atom-bound hydrogen is no greater than 300 ppm, per unit mass.

[10] A, oil-including silicone elastomer particle as set forth in any one of [1] through [9], wherein: the cross-linkable silicone composition used in the oil-including silicone elastomer particle is a cross-linkable composition that includes:

(a) an organopolysiloxane having at least two alkenyl groups, with a carbon number between 4 and 20, per molecule;

(b) an organohydrodiene polysiloxane having at least two silicon atom-bound hydrogen atoms per molecule; and arbitrarily (c) a hydrosilylation reaction catalyst, wherein:
the mole ratio of the alkenyl group inclusion proportion (Alk) of the component (a) and the silicon atom-bound hydrogen atom inclusion proportion (H) of the component (b) is in a range of:
H/Alk=0.7 through 1.2.

Moreover, the object of the present invention is achieved through a composition that includes the oil-including silicone elastomer particle described above, and the use thereof in specific applications. Specific examples thereof are as follows.

[11] A cosmetic raw material that includes an oil-including silicone elastomer particle as set forth in any one of [1] through [10].

[12] A cosmetic composition that includes an oil-including silicone elastomer particle as set forth in any one of [1] through [10].

[13] An organic resin additive that includes an oil-including silicone elastomer particle as set forth in any one of [1] through [10].

[14] An organic resin that includes an oil-including silicone elastomer particle as set forth in any one of [1] through [10].

[14-1] An organic resin as set forth in [14] that is a curable organic resin composition or a thermoplastic resin.

[14-2] An organic resin as set forth in [14] that is a coating or a coating agent.

Moreover, the object according the present invention is achieved through a method for manufacturing the oil-including silicone elastomer particle, described above.

[15] A method for manufacturing an oil-including silicone elastomer particle as set forth in any one of [1] through [10], including the following steps (I) and (II):

Step (I): a step for forming a cross-linkable silicone emulsion particle through emulsifying, in water, a mixture that includes:
a cross-linkable silicone composition (A) that includes:
(a) an organopolysiloxane having at least two alkenyl groups, with a carbon number between 4 and 20, per molecule;
(b) an organohydrodiene polysiloxane having at least two silicon atom-bound hydrogen atoms per molecule; and arbitrarily
(c) a hydrosilylation reaction catalyst, wherein:
the mole ratio of the alkenyl group inclusion proportion (Alk) of the component (a) and
the silicon atom-bound hydrogen atom inclusion proportion (H) of the component (b) is in a range of:
H/Alk=0.7 through 1.2; and
an oil (B) that is liquid at 40° C.; and Step (II): a step for producing an oil-including silicone elastomer particle through curing, in the presence of the (c) hydrosilylation reaction catalyst, the cross-linkable silicone emulsion particle that was produced in Step (I).

Effects of the Invention

The silicone elastomer particle according to the present invention, when mixed into a cosmetic composition, or the like, has low oil absorption, is superior in improving the effects of softness and the texture and feel in use as a cosmetic, and, when compared to a conventional silicone elastomer particle or oil-including silicone particle, suppresses agglomeration over time, and is superior in ease of handling, storage stability, and stability when blended as a cosmetic raw material, or the like. Moreover, the use of the oil-including silicone elastomer particle according the present invention enables provision of a cosmetic raw material, organic resin additive, or another application that includes the same. Moreover, cosmetics that are superior in feel in use, storage stability, and the like can be provided through a cosmetic composition that includes the oil-including silicone elastomer particle according to the present invention.

Most Preferred Forms for Carrying Out the Invention

The oil-including silicone elastomer particles according to the present invention, and, in particular, applications thereof that include a cosmetic raw material, along with a manufacturing method thereof, and a cosmetic composition and an organic resin (including a coating/coating agent) that includes the same, will be explained in detail below.

The oil-including silicone elastomer particle according to the present invention is provided with the distinctive feature of having a structure wherein oil that is liquid at 40° C. is included in the silicone elastomer particle, having a structure wherein at least two silicon atoms within the silicone elastomer particle are cross-linked through a silalkylene group having a carbon number of between 4 and 20. Here the silalkylene group is formed within the polysiloxane molecule through a cross-linking reaction of a higher alkenyl group, to form a polymer matrix of the silicone elastomer particle; however, the oil that is liquid at 40° C. preferably is included in advance in the cross-linkable particle at a stage prior to the cross-linking reaction, that is, at the stage of being a cross-linkable silicone composition particle that is a liquid that is a precursor for the oil-including silicone elastomer particle. When compared to the case wherein, for example, a prescribed amount of oil that is liquid at 40° C. is added, in a different step, to a solid silicone elastomer particle that has a structure that is cross-linked through silalkylene groups with carbon numbers between 4 and 20, this has the benefit of the oil absorption of the oil-including silicone elastomer particles produced, and especially oil absorption for silicone oil in particular, being less.

Preferably the oil-including silicone elastomer particle according the present invention is produced through curing the cross-linkable silicone emulsion particle through a cross-linking reaction, and, in particular, preferably the oil that is liquid at 40° C., included in the silicone elastomer particle, is derived from oil that is liquid at 40° C. that is included in the cross-linkable silicone emulsion particle, rather than being added after the cross-linking reaction. That is, preferably the oil-including silicone elastomer particle according the present invention is that which is cured after first forming, into emulsion particles, the mixture of the oil and the cross-linkable silicone composition.

Particularly preferably, the oil-including silicone elastomer particle is a silicone elastomer particle that is defined by the manufacturing process, produced through a cross-linking reaction, in water, of a cross-linkable silicone emulsion particle produced through emulsification, in water, a mixture of a cross-linkable silicone composition that includes at least an organopolysiloxane wherein there are at least two alkenyl groups, with carbon numbers between 4 and 20, within the molecule, and an oil that is liquid at 40° C., having a structure wherein at least two silicon atoms within the silicone elastomer particle are cross-linked through a silalkylene group with a carbon number between 4 and 20, to include, in the silicone elastomer particle, an oil that is liquid at 40° C. that is derived from the cross-linkable silicone emulsion particle.

Moreover, the oil-including silicone elastomer particle obtained through passing through such a manufacturing process, when used as a cosmetic raw material in particular, can further improve the appearance, spread, and feel of the cosmetic, and when compared to an oil-including silicone elastomer particle that includes the same amount of oil that is liquid at 40° C., the particles produced through the manufacturing method set forth above have a tendency to be able to solve well the problems according to the present invention. One ideal form for achieving the technological effects of the present invention, in this way, may be, and suitably is, defined through the manufacturing process.

The silicone elastomer particle according to the present invention has a structure wherein, within the particle, at least two silicon atoms are cross-linked by a silalkylene group with a carbon number between 4 and 20. Preferably this type of silalkylene cross-linking structure is formed through causing a hydrosilylation reaction of an alkenyl group with a carbon number between 4 and 20 and a silicon atom-bound hydrogen atom, between different siloxane molecules. In the present invention, preferably the silalkylene group that cross-links between a silicon atom within the siloxane that structures the silicone elastomer particle and another silicon atom is a silalkylene group with a carbon number between 4 and 16, where, more preferably, this carbon number is in a range between 4 and 8, where 6 (that is, a hexylene group) is particularly preferred.

Here, from the perspective of being able to control the agglomeration with the passage of time, the lipophilicity, and the storage stability of the oil-including silicone elastomer particles that are ultimately produced, and the perspective of oil absorption, preferably the silicone elastomer particles substantially do not include, within the particles, silalkylene groups of a carbon number of 3 or less. Here "substantially do not include" is that the proportion with which silalkylene groups of a carbon number of 3 or below are included in the particle is less than 5 mass % in respect to the silicone elastomer particle, and preferably less than 3 mass %, and particularly preferably less than 1 mass %, where most preferably the amount of raw materials that are added intentionally and that provide silalkylene groups with a carbon number of 3 or less is zero, that is, 0 mass %.

In particular, if silalkylene groups with carbon numbers of three or less, introduced through a hydrosilylation reaction with a vinyl group, for example, were to exist within the particle, the oil-including silicone elastomer particle produced would have a remarkable tendency for agglomeration over time, and, in particular, would be deficient in terms of storage stability and ease of handling when used as a cosmetic raw material. In particular, there would be a strong tendency for the oil-including silicone elastomer particles, when compared to silicone elastomer particles that do not include oil, to be soft and to be tacky, and oil-including elastomer silicone particles cross-linked by silalkylene groups having carbon numbers of three or less, derived from lower alkenyl groups such as, primarily, vinyl groups, or the like, are unusable unless stirring operations are carried out in advance of adding to the mixture, and cause the cosmetic composition to thicken or gellify after mixing, and have a worse feeling, through oil absorption, and the like, and thus are undesirable.

While in the oil-including silicone elastomer particle according the present invention there is no particular limitation on the average primary particle diameter, from the perspectives of applying a smooth feel and a good feeling in use to a cosmetic, of not causing visual flaws, and of storage stability and mixing stability as a cosmetic raw material, an average particle diameter in a range of between 0.5 and 20 μm, measured through a laser diffraction scattering technique, is preferred, and a range of between 0.5 and 15 μm is more preferred. Note that the particle diameters of the oil-including silicone elastomer particles can be controlled through the cross-linkable silicone emulsion particles and through a step for crushing or grading the oil-including silicone elastomer particles produced.

The shapes of the oil-including silicone elastomer particles according the present invention may be, for example, spheroidal, spherical, elliptical, or irregular, where spheroidal and spherical are particularly preferred. Spheroidal oil-including silicone elastomer particles can be produced easily through a method wherein a form of an aqueous solution, described below, is produced, and dried using a vacuum dryer, a hot air circulating oven, or a spray dryer.

The oil-including silicone elastomer particles according to the present invention have a structure wherein oil that is liquid at 40° C. is included inside and outside of the polymer matrix that is the elastic silicone elastomer polymer. On the other hand, as described above, the oil-including silicone elastomer particle according to the present invention is cured after forming a cross-linkable silicone composition, in a state that includes oil (a mixture of oil and a cross-linkable silicone) in the form of emulsion particles, and thus the oil-including silicone elastomer particles produced will be a structure wherein the oil is filled densely within the polymer matrix of the silicone elastomer, so measuring the hardness and softness thereof by isolating only the silicone elastomer particles from the two is difficult. However, from the perspective of designing and estimating the overall physical properties of the oil-including silicone elastomer particles, preferably the design and selection of the raw materials for the oil-including silicone elastomer particles is based on the physical properties of the silicone elastomer particles in a state that does not include the oil.

That is, preferably, in the present invention, when the cross-linkable silicone composition used in forming the silicone elastomer particles is cured into the form of a sheet in a state wherein the oil that is liquid at 40° C. is not included, the measurement by a JIS A hardness meter, as specified in JIS K6301, will be in a range of between 10 and 80. When the JIS-A hardness of a rubber sheet, measured through curing, in the form of a sheet, the cross-linkable silicone composition in a state wherein no oil is included is in the range set forth above, the oil-including silicone elastomer particles produced will have thoroughly suppressed agglomeration, and will tend to have fluidity and dispersibility, and will have a dry, smooth, soft feel, and, additionally, through selecting the JIS-A hardness as described above, the feeling in use and ease of handling can be designed and forecasted, to some degree, when mixing into cosmetics, and can improve the stress mitigating properties when mixed into an organic resin. The oil-including silicone elastomer particles according to the present invention, when used in a cosmetic raw material, a stress relaxing agent for an organic resin, or the like, preferably has a JIS-A hardness of between 30 and 80, where the use of silicone elastomer particles wherein this is in a range of between 50 and 80 is particularly preferred.

The silicone elastomer particles according the present invention further should have an inclusion proportion of silicon atom-bound hydrogen of no greater than 300 ppm, per unit mass. The silicon atom-bound hydrogen inclusion proportion more preferably is no greater than 250 ppm, and even more preferably no greater than 200 ppm. Moreover, no greater that 150 ppm is more preferred, and no greater than 100 ppm is even more preferred, and no greater than 50 ppm is even more preferred, and no greater than 20 ppm is even more preferred. In the silicone elastomer particles according to the present invention, if there were too much silicon atom-bound hydrogen, cross-linking reactions with the other reactive functional groups that remain within the silicone elastomer particles would advance, which would produce cohesion in the oil-including silicone elastomer particles as time elapses. Moreover, in the present invention, the production of flammable hydrogen gas as time elapses when these particles are stored is suppressed through reducing the silicon atom-bound hydrogen in the silicone elastomer particles so that no problems will arise such as swelling of the containers or ignition, so there will be the benefit of safety in handling when the oil-including silicone elastomer particles produced are used as a cosmetic raw material or in other applications.

Note that the method for measuring silicon atom-bound hydrogen in the silicone elastomer particles typically is a method that uses gas chromatography (the headspace method) after contact with alkali. For example, an ethanol solution of potassium hydroxide with a 40% concentration is added with equal amounts, in respect to unit mass, to the silicone elastomer particles, and after resting for one hour, the hydrogen gas that is produced up until the reaction endpoint is trapped, enabling identification through quantification through headspace gas chromatography, where the details thereof are disclosed in, for example, Patent Document 2, described above.

[Cross-Linkable Silicone Composition Used in Forming the Silicone Elastomer Particle]

The oil-including silicone elastomer particle according to the present invention has a structure wherein at least two silicon atoms per molecule are cross linked by a silalkylene group with a carbon number between 4 and 20, and can be cured, in the state of a mixture that includes an oil that is liquid at 40° C., through a hydrosilylation reaction of a cross-linkable silicone composition that includes the following components:

(a) an organopolysiloxane having at least two alkenyl groups, with a carbon number between 4 and 20, per molecule;

(b) an organohydrodiene polysiloxane having at least two silicon atom-bound hydrogen atoms per molecule; and (c) a hydrosilylation reaction catalyst, wherein:

the component (a) is an organopolysiloxane having at least two alkenyl groups, with a carbon number between 4 and 20, per molecule, where there is no particular limitation to the structure thereof, and the structure may be of one or more types selected from straight-chain types, cyclic types, network types, and straight-chain types having partial branches, and straight-chain organopolysiloxanes are particularly preferred. The viscosity of this component (a) preferably is a viscosity that enables dispersion of the cross-linkable composition, described above, into water, or a viscosity range that enables dispersion in a spray dryer, or the like. Specifically, preferably it is in a range of between 20 and 100,000 mPa·s, and particularly preferably in a range of between 20 and 10,000 mPa·s, at 25° C.

From the perspective of oil absorbency and dispersibility of the silicone elastomer particles, preferably the component (a) is a straight-chain organopolysiloxane wherein the inclusion proportion of dimethyl siloxane units expressed by the formula: —(CH$_3$)$_2$SiO— is no less than 90 mol % of all siloxane units other than the siloxane units that are the molecule terminators. Similarly, from the perspective of improving the oil absorption of the silicone elastomer particles produced, preferably the cyclic or straight-chain organopolysiloxanes with a low degree of polymerization (polymerization of between 3 and 20) are removed from component (a) in advance through stripping, or the like.

The alkenyl groups with a carbon number between 4 and 20 in component (a) may be, for example, butenyl groups, pentenyl groups, hexenyl groups, heptenyl groups, octenyl groups, nonenyl groups, decenyl groups, undecenyl groups, dodecenyl groups, tridecenyl groups, tetradecenyl groups, pentadecenyl groups, hexadecenyl groups, heptadecenyl groups, octadecenyl groups, nonadecenyl groups, icosenyl groups, or the like. From the perspective of reactivity and the perspective of cohesiveness, the carbon numbers of the alkenyl groups are between 4 and 16, and preferably in a range of between 4 and 8, and the use of a hexenyl group, which is an alkenyl group with a carbon number of 6, is particularly preferred. Moreover, preferably the alkenyl groups are on the ends of the molecular chains of the organopolysiloxanes, but they may instead be on side chains, or may be on both. As groups other than alkenyl groups that may be bonded to silicon atoms there are: alkyl groups such as methyl groups, ethyl groups, propyl groups, butyl groups, and the like; a cycloalkyl groups such as cyclopentyl groups, cyclohexyl groups, and the like; aryl groups such as phenyl groups, tolyl groups, xylyl groups, and the like; aralkyl groups such as benzyl groups, phenethyl groups, 3-phenyl propyl groups, and the like; and non-substituted or substituted monofunctional hydrocarbon groups such as halogenated alkyl groups such as 3-chloropropyl groups, 3,3,3-trifluoropropyl groups, and the like.

Preferably component (a) is a straight-chain organopolysiloxane expressed by Chemical Formula (1) below:

[CHEMICAL FORMULA 1]

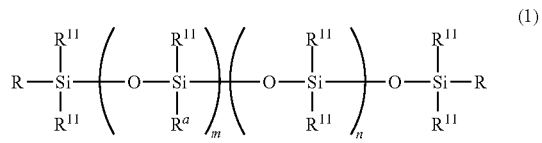

(1)

In Formula (1), $R^{11}$ each independently is an alkyl group with a number of carbon atoms of between 1 and 20 (for example, a methyl group, or the like), that is non-substituted or substituted with a halogen atom, an aryl group with between 6 and 22 carbon atoms (for example, a phenyl group, or the like), or a hydroxyl group, and, industrially, preferably is a methyl group or phenyl group. $R^a$ is an alkenyl group with a number of carbon atoms between 4 and 20, where a hexenyl group is particularly preferred. R is a group that is expressed by $R^{11}$ or $R^a$. m is a number that is no less than 0, where n is a number that is no less than 1. Note that m, n, and R are numbers such that the inclusion proportion of the vinyl (CH$_2$=CH—) part in the alkenyl group with the number of carbon atoms of between 4 and 12 in the organopolysiloxane molecule expressed by Formula (1), above, will be between 0.5 and 3.0 mass %, the viscosity of component (a) at 25° C. is between 20 and 10,000 mPa·s.

Particularly preferably, component (a) is an organopolysiloxane having hexenyl groups at both ends of the molecular chain and in a side chain, expressed by Chemical Formula (2), below:

[CHEMICAL FORMULA 2]

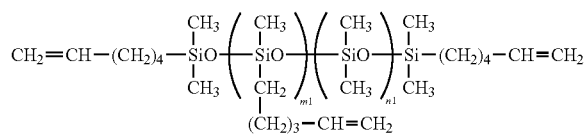

(In Formula (2), m1 is a number that is no less than 0, and n1 each is a positive number, wherein m1 is a number such that the inclusion proportion of the vinyl (CH2=CH—) part in the hexenyl groups (—(CH$_2$)$_4$CH=CH$_2$) of the molecule expressed by Formula (2) will be in a range of between 0.5 and 3.0 mass %, and more preferably in a range of between 1.0 and 2.0 mass %. Moreover, m1+n1 is a number in a range wherein the viscosity, at 25° C., of the organopolysiloxane expressed by Formula (2) will be no less than 20 mPa·s, and, more suitably, a number so that it will be between 100 and 500 mPa·s)

Preferably the (b) organohydrodiene polysiloxane having at least two silicon atom-bound hydrogen atoms per molecule is a cross-linking agent for component (a) and has at least three silicon atom-bound hydrogen atoms per molecule, where there is no particular limitation on the bonding positions of the hydrogen atoms within the molecule.

Organic groups that are bonded to silicon atoms, other than two hydrogen atoms, included in component (b) may be, for example, alkyl groups such as methyl groups, ethyl groups, propyl groups, butyl groups, octyl groups, and the like, but preferably are methyl groups. Moreover, the molecular structure of the organohydrodiene polysiloxane of component (b) may be, for example, a straight-chain structure, a branched structure, a branched cyclic structure, or a combination thereof. Note that the "number of silicon-bound hydrogen atoms within a single molecule" is the mean for all molecules.

The viscosity of component (b) at 25° C. is between 1 and 1000 mPa·s, and preferably between 5 and 500 mPa·s. This is because if the viscosity of component (b) at 25° C. were less than 1 mPa·s, there would be a tendency for component (b) to evaporate from within the cross-linkable composition wherein it is included, and if in excess of 1000 mPa·s, the curing time for the cross-linkable composition including such a component (b) would be too long, which could cause curing defects. While there is no particular limitation on such a component (b) it may be, for example, a both-end trimethyl siloxy group-blocked dimethyl siloxane-methyl hydrodiene siloxane copolymer, a both-end dimethyl hydrodiene siloxy group-blocked dimethyl siloxane-methyl hydrodiene siloxane copolymer, a both-end dimethyl hydrodiene siloxy group-blocked dimethyl polysiloxane, a both-end trimethyl siloxy group-blocked methyl hydrodiene polysiloxane, a cyclic methyl hydrodiene polysiloxane, a cyclic methyl hydrodiene siloxane-dimethyl siloxane copolymer, or the like.

Here preferably the H/Alk value that is the mole ratio of the alkenyl group inclusion proportion (Alk) of component (a) and the silicon atom-bound hydrogen atom inclusion proportion (H) of component (b) (=the reaction ratio in the hydrosilylation reaction), is in a range of between 0.7 and 1.2. Preferably the lower limit for this H/Alk is no less than 0.80, no less than 0.85, no less than 0.90, and no less than 0.95, where the upper limit is no greater than 1.15, and more preferably no greater than 1.10, or no greater than 1.05. If the upper limit for the H/Alk were greater than the values set forth above, there would be a tendency for non-reacted silicon atom-bound hydrogen atoms to remain after the reaction, and, conversely, if the H/Alk upper limit were less than the values described above, there would be a tendency for non-reacted alkenyl groups to remain after the reaction. Because these are the curing reactive groups, if large amounts thereof were to remain within the particles, this would cause cross-linking reactions between particles with the passage of time, which could result in cohesion between the oil-including silicone elastomer particles produced, or in dispersion defects, and, additionally, if there were residual reactive hydrogen atoms, this could cause the production of flammable hydrogen gas with the passage of time. Particularly preferably, with H/Alk values in the range of between 0.9 and 1.1, and particularly, near to 1.0, the curing reactive groups will be consumed completely, terminating the cross-linking reaction, which can suppress effectively cohesion between particles over time.

The component (c) is a hydrosilylation reaction catalyst, a catalyst for promoting an addition reaction (hydrosilylation reaction) between the silicon atom-bonded alkenyl groups that exist in the cross-linkable composition and the silicon atom-bonded hydrogen atoms. Preferably the hydrosilylation reaction catalyst is a hydrosilylation reaction catalyst that includes a platinum-based metal, and specifically may be, for example, chloroplatinic acid, an alcohol-modified chloroplatinic acid, an olefin complex of chloroplatinic acid, a complex of chloroplatinic acid and a ketone, a complex of chloroplatinic acid and a vinyl siloxane, platinum tetrachloride, a platinum ultra powder, that wherein solid platinum is carried on an alumina or silica carrier, platinum black, an olefin complex of platinum, an alkynyl siloxane complex of platinum, a carbonyl complex of platinum, a platinum-based catalyst of a thermoplastic organic resin powder such as a methyl methacrylate resin, a carbonate resin, a polystyrene resin, or a silicone resin that includes any of the aforementioned platinum-based catalysts, or the like. In particular, complexes of chloroplatinic acid with divinyltetramethyldisiloxane, complexes of chloroplatinic acid with tetramethyltetravinylcyclotetrasiloxane, platinum divinyltetramethyldisiloxane complexes, platinum tetramethyltetravinyl chlorotetrasiloxane complexes, and other platinum alkenyl siloxane complexes can be used preferentially. Note that the catalyst for promoting the hydrosilylation reaction may instead be a non-platinum-based metal catalyst, such as iron, ruthenium, iron/cobalt, or the like.

The amount of component (c) to add to the cross-linkable composition should be a catalytic amount, where normally it should be an amount such that the amount of platinum-based metal included in the component (c) is in a range of between 1 and 1000 ppm in respect to the total mass of the cross-linkable composition, described above, where an amount such that this amount of platinum-based metal will be in a range of between 5 and 500 ppm is even more preferred. Note that the amount of platinum metal in the silicone elastomer particles may be reduced through the method proposed by the present inventor in Japanese Unexamined Patent Application Publication 2014-122316.

The timing with which composition (c) is added to the cross-linkable composition may be selected depending on the method for forming the oil-including silicone elastomer particles, and may be through addition into the composition in advance, or in a form wherein it is supplied from a spray line that is different from that for component (a) or component (b), adding to either and mixing during spraying. The oil-including silicone elastomer particles according to the present invention preferably pass through an aqueous suspension that is formed through passing through emulsification in water, where the component (c) may be added to the cross-linkable silicone composition in advance, or an emulsion that includes the component (c) may be added into the water separately.

The cross-linkable silicone composition described above may include a curing inhibiting agent that is typical with a hydrosilylation reaction inhibiting agent. This curing retarding agent may be, for example, an acetylene-based compound, and enyne compound, an organic nitrogen compound, an organic phosphorous compound, or an oxime compound. As specific compounds there are, for example, alkene alcohols such as 2-methyl-3-butyn-2-ol, 3,5-dimethyl-1-hexyne-3-ol, 3-methyl-1-pentyn-3-ol, 2-phenyl-3-butyn-2-ol, 1-ethynyl-1-cyclohexanol (ETCH), and the like; enyne compounds such as 3-methyl-3-trimethylsiloxy-1-butyne, 3-methyl-3-trimethylsiloxy-1-pentyne, 3,5-dimethyl-3-trimethylsiloxy-1-hexyne, 3-methyl-3-pentene-1-yne and 3,5-dimethyl-3-hexene-1-yne, and the like; and alkenyl siloxanes such as 1-ethynyl-1-trimethylsiloxycyclohexane, bis (2,2-dimethyl-3-butynoxy) dimethylsilane, methyl (tris (1,1-dimethyl-2-propynyloxy)) silane, 1,3,5,7-tetramethyl-1,3,5,7-tetravinylcyclotetrasiloxane and 1,3,5,7-tetramethyl-1,3,5,7-tetrahexenylcyclotetrasiloxane. The amount thereof to be added is in a range of between 0.001 and 5 parts by weight per 100 parts by weight of component (a), but may be designed as appropriate depending on, for example, the type of retarding agent used, the characteristics and amount of the hydrosilylation reaction catalyst used, and the like.

For the reasons set forth above, preferably the cross-linkable silicone composition substantially does not include, and particularly preferably completely excludes, organopolysiloxanes having alkenyl groups with carbon numbers of three or less, in addition to the component (a). The oil-including silicone elastomer particles that are ultimately produced would not adequately solve the problem in the present invention with a composition wherein cross-linked products would be produced with silalkylene groups with carbon numbers of three or less, derived from alkenyl groups having these low carbon numbers, if they were to exist at 5 mass % or more within the particles.

The cross-linkable silicone composition may include components other than the components described above in a range wherein the technological effect of the present invention is not lost. For example, it may include: aliphatic hydrocarbons such as n-hexane, cyclohexane, n-heptane, and the like; aromatic hydrocarbons such as toluene, xylene, mesitylene, and the like; ethers such as tetrahydrofuran, dipropyl ether, and the like; organic solvents such as ketones such as acetone, methyl ethyl ketone, methyl isobutyl ketone, and the like; antioxidants such as phenols, quinones, amines, phosphites, phosphites, sulfites, thioethers, and the like; optical stabilizers such as triazoles, benzophenones, and the like; flame retarding agents such as phosphates, halogens, phosphors, antimonys, and the like; antistatic agents, such as cationic surfactants, anionic surfactants, and/or nonionic surfactants; dyes; pigments; and so forth.

[Oil that is Liquid at 40° C.]

The oil-including silicone elastomer particle according the present invention has a structure that includes an oil that is liquid at 40° C., within the silicone elastomer particle formed through the cross-linking reaction of the cross-linkable silicone composition, described above. Preferably this oil that is liquid at temperatures between room temperature and 40° C. is derived from the cross-linkable silicone emulsion particles in the process of forming the oil-including silicone elastomer particles, and through being present in the precursor to the polymer matrix from prior to formation of the cross-linked structure in forming the silicone elastomer particle, can apply low oil absorption to the oil-including silicone elastomer particles of the present invention and can further prevent agglomeration with the passage of time, improving storage stability and ease of handling. Moreover, the oil-including silicone elastomer particles according the present invention, including the desired liquid oil in the soft silicone elastomer particles, can apply a better texture, feeling in use, and external appearance to the cosmetics, when compared to silicone elastomer particles alone or to a composition wherein the oil is added to the silicone elastomer particles later.

Being "liquid at 40° C." means that the oil has fluidity at 40° C., where a liquid oil that has fluidity at a lower temperature, such as, for example, 25° C., is included explicitly in the range of "oil that is liquid at 40° C." in the present invention. Here the "oil having fluidity" means that after the fluid surface of the oil has become horizontal within a prescribed container, the fluid surface can become horizontal again after one hour if the container is inclined. Here "horizontal" means that a plane is formed that crosses, at a right angle, the direction in which gravity acts. On the other hand, the oil that is liquid at 40° C. in the present invention may be in a solid or semisolid form at room temperature (25° C.), and may be an oil that has fluidity in a state wherein it has been heated to 40° C. (for example, a wax that flows when heated). In this way, the oil that is included in the oil-including silicone elastomer particles in the present invention may, in the fluidity thereof, be a liquid wherein the viscosity is adjusted to a range of between low viscosity and high viscosity, and may be selectable in a broad range that is in the form of a wax or a solid at room temperature and becomes a liquid at 40° C., and may be a single type of oil or a mixture of two or more types. For example, an oil mixture wherein, for example, an oil that is between high viscosity and a viscosity-adjusted rubber-type oil is mixed and dispersed uniformly into a low viscosity oil is explicitly included in the range of "an oil that is liquid at 40° C." in the present invention.

The overall viscosity of the oil that is liquid at 40° C., according to the present invention (the simple viscosity if a single type of oil, or the mixture viscosity if a mixture of two or more types of oil) preferably is in a range of between 1.0 and 10,000,000 mPa·s at 40° C., and more preferably in a range between 1.0 and 1,000,000 mPa·s. Moreover, it may be such an oil having a viscosity in a range of between 1.5 and 1,000,000 mPa·s at a temperature of either 25° C. or 40° C. If the overall viscosity of the oil is within the range set forth above, then, in the process for forming the oil-including silicone elastomer particles according to the present invention, cross-linkable silicone emulsion particles produced through emulsification in water of a mixture of the cross-linkable silicone composition and oil that is liquid at 40° C. can be produced relatively easily. Note that when emulsifying the oil that is liquid at 40° C., the oil that is solid at room temperature (25° C.) may, and preferably is, emulsified in a state wherein it is melted through heating to at least 40° C.

The inclusion proportion of oil that is liquid at 40° C., in the oil-including silicone elastomer particle according the present invention, may be selected as appropriate depending on the characteristics of the particle that is desired, and, in practice, is in a range of between 5 and 60 mass % in respect to the particle as a whole, and preferably in a range of between 5 and 50 mass %, and more preferably in a range of between 10 and 45 mass %. If the inclusion proportion of the oil that is liquid at 40° C. were to exceed the upper limit set forth above, there would be effusion of the oil from the particles, which could produce tackiness, and it might not be possible to achieve the desired feel in use if mixed into a cosmetic. On the other hand, if the inclusion proportion of oil that is liquid at 40° C. were to be less than the lower limit set forth above, the amount of oil in the silicone elastomer particles would be too little, and it might not be possible to achieve completely the technological effects of having low oil absorption and suppression of agglomeration with the passage of time.

The oil-including silicone elastomer particle according the present invention may be in a form that is a mixture of different types or inclusion proportions of liquid oils. Such particles can be produced through mixing different oil-including silicone elastomer particles that were prepared separately, or may be produced through preparing, and mixing in different compositions, the cross-linkable silicone emulsion particles that are the precursors thereof, and then curing thereafter.

Preferably the oil that is liquid at 40° C. in the present invention is a non-reactive oil that does not include reactive functional groups in the molecules. Here "reactive functional groups" are functional groups that substantially do not contribute to the cross-linking reaction of the cross-linkable silicone composition, and it is particularly preferable that there be no functional groups for hydrosilylation reactions selected from functional groups that include unsaturated hydrocarbon groups that have carbon-carbon double bonds, and from silicon atom-bound hydrogen atoms. If reactive functional groups were included in the oil, the cross-linking structure of the siloxane for structuring the silicone elastomer polymer and the oil would form a combined structure through shared bonds, which could prevent achievement of the technological effects that derive from the structure wherein non-reacted oil is included densely the silicone elastomer particle, for example, characteristics such as applying the feeling in use, softness, low oil absorption, and the like, to cosmetics.

The oil that is liquid at 40° C. preferably is an oil that can be applied to cosmetics, and may use one or more selections from (D1) silicone-based oils and (D2) organic oils. Specific examples thereof are given below. In particular, silicone oils, hydrocarbon oils, and ester oils, which do not include reactive functional groups within the molecules, are more preferred from the perspective of feeling in use of the cosmetics into which the oil-including silicone elastomer particles are mixed.

(D1) Silicone-Based Oils

Typically silicone-based oils are hydrophobic, and the molecular structures thereof may be straight, cyclic, or branched. The molecular structure thereof may be straight, cyclic, or branched. Normally the viscosity of the silicone oil at 40° C. is in a range of between 0.65 and 100,000 mm²/sec, and preferably in a range of between 0.65 and 10,000 mm²/sec. Moreover, the silicone-based oil may be, and preferably is, volatile.

The silicone oil specifically may be a cyclic organopolysiloxane, a straight-chain organopolysiloxane, or a branched organopolysiloxane. Of these, a volatile straight organopolysiloxane, branched organopolysiloxane, or cyclic organopolysiloxane is preferred.

The silicone oil may use, for example, an organopolysiloxane that is represented by general formula (3), (4), or (5), below:

[CHEMICAL FORMULA 3]

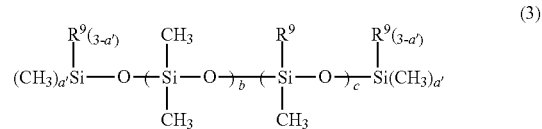
(3)

(In this formula, $R^9$ is a selection from hydrogen atoms, hydroxyl groups, or alkyl groups, aryl groups, alkoxy groups, and groups expressed by $(CH_3)_3SiO\{(CH_3)_2SiO\}_I Si(CH_3)_2CH_2CH_2-$ (wherein I is an integer of between 0 and 100), with a carbon number between 1 and 30 and which is monohydric unmodified or fluorine or amino-modified, where a' is an integer of between 0 and 3, b is an integer of between 0 and 1000, and c is an integer of 0 through 1000, and wherein 1 b+c 2000.)

[CHEMICAL FORMULA 4]

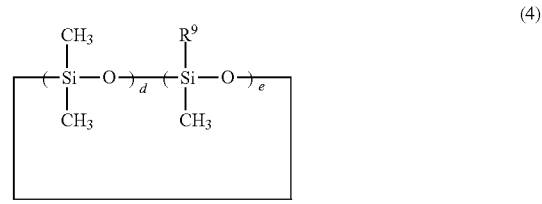
(4)

(In this formula, $R^9$ is the same as described above, d is an integer of between 0 and 8, e is an integer of between 0 and 8, and $3 \leq d+e \leq 8$.)

[Chemical Formula 5]

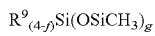
(5)

(In this formula, $R^9$ is the same as described above, f is an integer of between 1 and 4, and g is an integer of between 0 and 500.)

The alkyl group, aryl group, or alkoxy group that is monohydric non-modified or fluorine or amino modified, with a carbon number of between 1 and 30 may be, for example, a straight or branched alkyl group with a carbon number of between 1 and 30 such as a methyl group, an ethyl group, a propyl group, a butyl group, a pentyl group, a hexyl group, a heptyl group, an octyl group, a decyl group, a dodecyl group, a dodecyl group, or the like; a cycloalkyl group with a carbon number of between 3 and 30, such as a cyclopentyl group, a cyclohexyl group, or the like; an aryl group with a carbon number of between 6 and 30, such as a phenyl group, a tolyl group, a xylyl group, a naphthyl group, or the like; an alkoxy group with a carbon number between 1 and 30 such as a methoxy group, an ethoxy group, a propoxy group, or the like; or a group in which the hydrogen atoms attached to the carbon atoms of these groups are at least partially replaced by fluorine or by amino groups. Preferably it is a non-modified alkyl group or an aryl group, and more preferably a non-modified alkyl group or aryl group with a carbon number of between 1 and 6, and particularly preferably is a methyl group, an ethyl group, or a phenyl group.

More specifically, the silicone oil having these structures may be, specifically, a cyclic organopolysiloxane, octamethylcyclotetrasiloxane, decamethylcyclopentasiloxane, dodecamethylcyclohexa-siloxane, 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris (3,3,3-trifluoropropyl) trimethycyclotrisiloxane, 1,3,5,7-tetra (3-methacryloxypropyl) tetramethylcyclotetrasiloxane, 1,3,5,7-tetra (3-acryloxypropyl) tetramethylcyclotetrasiloxane, 1,3,5,7-tetra (3-carboxypropyl) tetramethylcyclotetrasiloxane, 1,3,5,7-tetra (3-vinyloxypropyl) tetramethylcyclotetrasiloxane, 1,3,5,7-tetra (p-vinylphenyl) tetramethylcyclotetrasiloxane, 1,3,5,7-tetra [3-(p-vinylphenyl) propyl] tetramethylcyclotetrasiloxane, 1,3,5,7-tetra (N-acryloyloyl-N-methyl-3-aminopropyl) tetramethylcyclotetrasiloxane, 1,3,5,7-tetra (N,N-bis(lauroyl)-3-aminopropyl) tetramethylcyclotetrasiloxane, or the like.

The straight-chain organopolysiloxane, the straight-chain organopolysiloxane may be, for example, a dimethylpolysiloxane with both ends of the molecular chain trimethylsiloxylated (a dimethylsiloxane of low viscosity such as 2 mPa·s and 6 mPa·s, etc. to high viscosity such as 1,000,000 mPa·s, or the like), a methylphenyl polysiloxane with both ends of the molecular chain trimethylsiloxylated, a copolymer of methylphenylsiloxane and dimethylsiloxane with both ends of the molecular chain trimethylsiloxylated, a diphenyl polysiloxane with both ends of the molecular chain trimethylsiloxylated, a copolymer of diphenylsiloxane and dimethylsiloxane with both ends of the molecular chain trimethylsiloxylated, trimethylpentaphenyltrisiloxane, phenyl (trimethylsiloxyl) siloxane, a methylalkyl polysiloxane with both ends of the molecular chain trimethylsiloxylated, a copolymer of a methylalkylsiloxane and dimethylsiloxane with both ends of the molecular chain trimethylsiloxylated, a copolymer of methyl (3,3,3-trifluoropropyl) siloxane and dimethylsiloxane with both ends of the molecular chain trimethylsiloxylated, α,ω-dihydroxypolydimethylsiloxane, α,ω-diethoxypolydimethylsiloxane, 1,1,1,3,5,5,5-heptamethyl-3-octyl trisiloxane, 1,1,1,3,5,5,5-heptamethyl-3-dodecyl trisiloxane, 1,1,1,3,5,5,5-heptamethyl-3-hexadecyl trisiloxane, tris-trimethylsiloxysiloxysilane, tris-trimethylsiloxysiloxysilane, tetraxtrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, a higher alkoxy-modified silicone, a fatty acid-modified silicone, a polyether-modified silicone, a higher alkyl-modified silicones with 8 or more carbon atoms, or the like.

The branched organopolysiloxane may be methyl trimethylsiloxysilane, ethyl trimethylsiloxysilane, propyl trimethylsiloxysilane, tetraxtrimethylsiloxysilane, phenyl trimethylsiloxysilane, or the like.

When the oil-including silicone elastomer particle according the present invention is used as a cosmetic raw material, if at least one of these types of silicone-based oils is included, this can improve stability with the passage of time, and can achieve a crisp, refreshing feel that is unique to silicone oil. More preferably, of the silicone-based oils described above, a decamethyl cyclopentasiloxane or modified or non-modified straight-chain organopolysiloxane wherein the viscosity is in a low viscosity range of between 2 and 500 mPa·s, 1,1,1,3,5,5,5-dimethyl-3-octyltrisiloxane (also known as "caprylyl methicone"), tristrimethyl siloxymethyl silane (also known as "M3T"), trimethyl pentylphenyltrisiloxane, polyether-modified silicone, or a higher alkyl modified silicone with a carbon number of no less than 8, or the like, is used.

(D2) Organic Oil

The organic oil typically is a (D2-1) hydrocarbon oil, an (D2-2) ester oil, a higher fatty acid, an oil or fat, or a fluorine-based oil, and in the present invention, when these are used, either singly or in mixtures, there is no particular limitation thereon insofar as the oil is a liquid at 40° C. Moreover, a hydrocarbon oil and/or an ester oil is preferred. These may be used either singly or in parallel, and may be used in parallel also with a silicone-based oil as described above. A combination of appropriate oils can improve the stability of the composition and/or cosmetic with the passage of time, and can apply the feel that is required for the given cosmetic. Mixing with a silicone-based oil as described above can apply the crisp, refreshing feel that is unique to silicone oil, and the use of a highly volatile oil can apply a crisp, refreshing feel on the skin, and, in addition, the use of a hydrocarbon oil and/or a fatty acid ester oil in parallel with the silicone oil can provide a feeling of moisture retention (also termed a "moist feel") and smooth feel as if the skin or hair were wet.

The (D2-1) hydrocarbon oil may be, for example, liquid paraffin, light liquid isoparaffin, heavy liquid isoparaffin, vaseline, n-paraffin, isoparaffin, isodododecane, iso-hexadecane, polyisobutylene, hydrogenated polyisobutylene, polybutene, ozokerite, cerecin, microcrystalline wax, paraffin wax, polyethylene wax, polyethylene-polypyrrolein wax, squalane, squalene, pristane, polyisoprene, or the like.

The (D2-2) ester oil may be, for example, hexyl decyl octanoate, cetyl octanoate, isopropyl myristate, isopropyl palmitate, butyl stearate hexyl laurate, myristyl myristate, oleyl oleate decyl oleate octyldodecyl myristate, hexyl decyl dimethyl octanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylhexanoate trimethylol propane, triethylhexanoate ditrimethylol propane, (isostearic acid/sebacic acid) ditrimethylol propane, trimethylol propane trioctanoate, trimethylol propane triisostearate, diisopropyl adipate, diisobutyl adipate, adipic acid 2-hexyl decyl adipate, adipic acid di-2-heptyl undecyl adipate, diisostearyl malate, hydrogenated monoisostearic acid castor oil, N-alkyl glycol monoisostearate, octyldodecyl isostearate, isopropyl isostearate, isocetyl isostearate, di-2-ethylhexanoic acid ethylene glycol, cetyl 2-ethylhexanoate, pentaerythritol tetra-2-ethylhexanoate, octyldodecylgum esters, ethyl oleate, octyldodecyl oleate, neopentyl glycol dicaprate, triethyl citrate, 2-ethylhexyl succinate, dioctyl succinate, isocetyl stearate, diisopropyl sebacate, sebacic acid di-2-ethylhexyl sebacate, diethyl sebacate, dioctyl sebacinate, dibutyl-octyl sebacinate, cetyl palimic acid, octyldodecyl palmitate, octyl palmitate, 2-ethylhexyl palmitate, 2-hexyl palmitate decyl palmitate, 2-heptyl undecyl palmitate, cholesteryl 12-hydroxystearylate, dipentaerythritol fatty acid esters, 2-hexyl decyl myristate, ethyl laurate, N-lauroyl-L-glutamic acid-2-octyldodecyl ester, N-lauroyl-L-glutamate di (cholesteryl/behenyl/octyldodecyl)N-lauroyl-L-glutamic acid di (cholesteryl/octyldodecyl) N-lauroyl-L-glutamate di (phytosteryl/behenyl/octyldodecyl)N-lauroyl-L-glutamate di (phytosteryl/octyldodecyl)N-lauroyl sarcosine isopropyl, diisostearyl malate, neopentyl glycol dioctanoate, isodecyl neopentanoate, isotridecyl neopentanoate, isostearyl neopentanoate, isononoate isononyl isononoate, isotridecyl isononoate, octyl isononanoate, isotridecyl isonononate, diethyl pentanediol dineopentanoate, methylpentanediol dineopentanoate, octyldodecyl neodecanoate, 2-butyl-2-ethyl-dioctanoic acid-2-ethyl-1,3-propanediol, pentaerythrityl tetraoctanoate, hydrogenated rosin pentaerythrityl, pentaerythrityl triethylhexanoate, (hydroxystearic acid/stearic acid/rosinic acid) dipentaerythrityl, polyglyceryl tetriisostearate, polyglyceryl nonaisostearate-10 deca (erucaic acid/isostearic acid/ricinoleic acid) polyglyceryl-8, (hexyl decanoic acid/sebacic acid) diglyceryl oligoester, glycol distearate (ethylene glycol distearate), diisopropyl dimer dilinoleate, diisostearyl dimer dilinoleate, dimer dilinoleic acid (isostearyl/phytosteryl) dimer dilinoleic acid (phytosteril/behenyl) dimer dilinoleic acid (phytosteryl/isostearyl/cetyl/stearyl/behenyl) dimer dilinoleil dimer dilinoleate, dimeric diinoleil iisostearate, dimer dilinorail hydroxylated rosin condensate, dimer linoleic acid cured castor oil, hydroxyalkyl dimer dilinolyl ether, glyceryl triisooctanoate, glyceryl triisostearate, glyceryl trimyristate, glyceryl triisopalmitate, glyceryl trioctanoate, glyceryl trioleate, glyceryl diisostearate, tris (caprylic/capric acid) glyceryl, tris (caprylic/capric/capric/myristic/stearic acid) glyceryl, hydrogenated rhodine triglycerides (hydrogenated ester gum) lysine triglycerides (ester gum) glyceryl behenate eicosan diacetate, glyceryl di-2-heptyl undecanoate, diglyceryl isostearate myristate, cholesteryl acetate, cholesteryl nonanoate, cholesteryl stearate, cholesteryl isostearate, cholesteryl oleate, cholesteryl 12-hydroxystearate, macadamia nut oil fatty acid cholesteryl, macadamia nut oil fatty acid phytosteril, phytosteryl isostearate, soft lanolin fatty acid cholesteryl, hard lanolin fatty acid cholesteryl, long chain branched fatty acid cholesteryl, long chain alpha hydroxy fatty acid cholesteryl, octyldodecyl ricinoleate, lanolin fatty acid octyldodecyl, octyldodecyl erceate, isostearate cured castor oil, avocado oil fatty acid ethyl esters, lanolin fatty acid isopropyl, or the like. Lanolin or a lanolin derivative may also be used as the ester oil.

In addition to the above, oils and fats, higher alcohols, higher fatty acids, fluorine-based oils, and the like, may be used as the oil, and two or more of these may be used in parallel. For example, two or more types of oils expressed below may be used in parallel. More specific examples of other oils that can be used in the present invention will be given below. Specifically, one or more selections from oils and fats, higher alcohols, higher fatty acids, and fluorine-based oils may be used, for example.

The oils and fats may be natural and/or vegetable oils and fats, or may be, as semi-synthetic oils and fats, avocado oil, flaxseed oil, almond oil, insect wax, enoil, olive oil, cacao fat, kapok wax, kaya oil, carnauba wax, liver oil, candelilla wax, beef tallow neats-foot fat, beef bone fat, hardened beef tallow, hydrangea oil, whale law, hardened oil, wheat germ oil, sesame oil, rice germ oil, rice bran oil, sugarcane wax, sasanqua oil, safflower oil, shea butter, sinagiri oil, cinnamon oil, jojoba wax, olive squalane, shellac wax, turtle oil, soybean oil, tea seed oil, camellia oil, evening primrose oil, corn oil, pork fat, rape seed oil, Japanese *paulownia* oil, bran wax, germ oil, horse fat, persic oil, palm oil, palm kernel oil, castor oil, hardened castor oil, castor oil fatty acid methyl ester, sunflower oil, grape oil, bayberry wax, jojoba oil, hydrogenated jojoba esters, macadamia nut oil, yellow bees wax, mink oil, cottonseed oil, cotton wax, Japan wax, mulberry kernel oil, montan wax, coconut oil, hardened coconut oil, tricyclic fatty acid glycerides, sheep fat, peanut oil, lanolin, liquid lanolin, reduced lanolin, lanolin alcohol, hard lanolin, lanolin acetate, lanolin fatty acid isopropyl, POE lanolin alcohol ether, POE lanolin alcohol acetate, lanolin fatty acid polyethylene glycol, POE hydrogenated lanolin alcohol ether, egg yolk oil, and the like. Note that "POE" means "polyoxyethylene."

A "higher alcohol" is, for example, a higher alcohol with a carbon number of between 10 and 30. Preferably the higher alcohol is a saturated monohydric aliphatic alcohol, where the part that is the hydrocarbon group may be either straight or branched, although straight is more preferred. The higher-level alcohol with a carbon number of between 10 and 30 may be, for example, lauryl alcohol, myristyl alcohol, palmithyl alcohol, stearyl alcohol, behenyl alcohol, hexadecyl alcohol, oleyl alcohol, isostearyl alcohol, hexyldodecanol, octyldodecanol, cetostearyl alcohol, 2-decyl tetradecinol, cholesterol, sitosterol, phytosterol, lanosterol, lanolin alcohol, hydrogenated lanolin alcohol, POE cholesterol ether, monostearyl glycerol ether (batyl alcohol), mono-oleyl glyceryl ether (selachyl alcohol), or the like.

The higher fatty acid may be, for example, lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, 12-hydroxystearic acid, or the like.

The fluorine-based oil may be, for example, perfluoropolyether, perfluorodecalin, perfluorooctane, or the like.

[Hardness of the Oil-Including Silicone Elastomer]

As described above, although direct measurement of the oil-including silicone elastomer particle is not possible, the hardness can be measured indirectly through curing the raw material, which is a mixture of the cross-linkable silicone composition that is used in forming the silicone elastomer particles, and the oil that is liquid at 40° C. Specifically, the cross-linkable silicone composition and the oil that is liquid at 40° C. is cured in a sheet without emulsification in water, and the hardness can be measured for the oil-including silicone elastomer sheet using the JIS A hardness meter that is specified in JIS K6301. The hardness of the oil-including silicone composition will differ depending on the type of the cross-linking silicone composition and the type and inclusion proportion of the oil that is liquid at 40° C., but preferably is in a range of between about 1 and 70. Note that generally the hardness of the oil-including silicone elastomer is less than the JIS-A hardness of a rubber sheet that is measured after curing, in a sheet, the cross-linkable silicone composition in a state that does not include oil, and exhibits characteristics that are softer.

[Formation of the Oil-Including Silicone Elastomer Particle and Manufacturing Method Thereof]

For the oil-including silicone elastomer particle according to the present invention, the method may include a step for curing, in the presence of the (c) hydrosilylation reaction catalyst, a cross-linkable silicone emulsion particle that is an emulsion in water of a mixture of oil that is a liquid at 40° C. and a cross-linkable silicone composition used for forming the silicone elastomer particle, described above, to produce a spherical oil-including silicone elastomer particle.

More specifically, the oil-including silicone elastomer particle according the present invention may be, and preferably is, prepared using a manufacturing method that includes the steps (I) and (II), below:

Step (I):
  A step for forming a cross-linkable silicone emulsion particle through emulsifying, in water, a mixture that includes:
  a cross-linkable silicone composition (A) that includes:
    (a) an organopolysiloxane having at least two alkenyl groups, with a carbon number between 4 and 20, per molecule;

(b) an organohydrodiene polysiloxane having at least two silicon atom-bound hydrogen atoms per molecule; and arbitrarily
(c) a hydrosilylation reaction catalyst, wherein:
the mole ratio of the alkenyl group inclusion proportion (Alk) of the component (a) and the silicon atom-bound hydrogen atom inclusion proportion (H) of component (b) is in a range of:
H/Alk=0.7 through 1.2; and
an oil (B) that is liquid at 40° C.; and
Step (II):
a step for producing an oil-including silicone elastomer particle through curing, in the presence of the (c) hydrosilylation reaction catalyst, the cross-linkable silicone emulsion particle that was produced in Step (I).

The cross-linkable silicone composition and the oil that is liquid at 40° C., used in forming the silicone elastomer particles, can be mixed uniformly using mechanical forces of, for example, a mixer. Moreover, the proportion with which oil is included in the oil-including silicone elastomer particle produced can be adjusted through adjusting the mixing proportions.

In this method, the oil-including silicone elastomer particles can be produced through curing after emulsification, in a surfactant aqueous solution, the mixture, described above, that includes the cross-linkable silicone composition and the oil that is liquid at 40° C. (termed, in this paragraph, the "cross-linkable mixture"). Moreover, the particle size can be adjusted easily through adjusting the diameters of the emulsified particles. The surface activating agent may be non-ionic, anionic, cationic, or betaine-based, for example. The particle sizes of the silicone elastomer particles produced will vary depending on the type of surface activating agent and the inclusion proportion thereof. To prepare silicone elastomer particles with small particle sizes, preferably the amount of added surface activating agent is in a range of between 0.5 and 50 parts by weight in respect to 100 parts by weight of the cross-linkable mixture. On the other hand, in order to prepare oil-including silicone elastomer particles with a large particle size, preferably the amount of the surface activating agent added is in a range of between 0.1 and 10 parts by weight in respect to 100 parts by weight of the cross-linkable mixture. Note that the amount of water added as the dispersing agent preferably is in a range of between 20 and 1500 parts by weight, or between 50 and 1000 parts by weight, in respect to 100 parts by weight of the cross-linkable mixture.

Preferably an emulsifier is used to disperse uniformly, into the water, the mixture, described above, that includes the cross-linkable silicone composition and the oil that is liquid at 40° C., doing so in the form of cross-linkable silicone emulsion particles. The emulsifier may be, for example, a homomixer, a paddle mixer, a Henschel mixer, a homo disper, a colloid mill, a propeller stirring apparatus, a homogenizer, an in-line-type continuous emulsifier, an ultrasonic emulsifier, a vacuum-type frozen mixer, or the like.

Next the aqueous dispersion of the cross-linkable silicone particles, prepared using the method described above, is allowed to rest while heating or at room temperature, to cure the cross-linkable silicone emulsion particles that are dispersed in the water, enabling preparation of an aqueous dispersion of oil-including silicone elastomer particles. When heating this aqueous dispersion, preferably the heating temperature is no more than 100° C., and between 10 and 95° C. is particularly preferred. Moreover, the method for heating the aqueous dispersion that includes the cross-linkable silicone emulsion particles may be, for example, a method wherein the aqueous dispersion is heated directly, a method wherein the aqueous dispersion is added to hot water, or the like. The liquid cross-linkable silicone emulsion particles are cured, through this cross-linking in the water, to form an aqueous dispersion of oil-including silicon elastomer particles.

The oil-including silicone elastomer particles according to the present invention, thus produced, can be used as-is as an aqueous dispersion (aqueous suspension). In particular, it may, and preferably is, used in the form of an aqueous suspension in a cosmetic raw material, or the like. When the aqueous solution is mixed into a cosmetic (such as a hair product, or the like) as a dispersing medium, the oil-including silicon elastomer particles according the present invention may be mixed in as an aqueous solution to enable easy uniform dispersion of the oil-including silicone elastomer particles, making it possible to achieve the desired performance and feeling in use.

The oil-including silicone elastomer particles according to the present invention are isolated through removal of water from the aqueous dispersion of the oil-including silicone elastomer particles. The method for removing the water from the aqueous dispersion may be, for example, a method that uses a vacuum dryer, a hot air circulating oven, or a spray dryer. Note that the heating/drying temperature of the spray dryer must be set as appropriate based on the thermal durability of the oil-including silicone elastomer particles, the cross-linking temperature, and the like. Note that preferably the temperature of the oil-including silicone elastomer particles is controlled so as to be no greater than the glass transition temperature thereof, in order to prevent secondary cohesion of the microparticles produced. The oil-including silicone elastomer particles obtained in this way may be recovered through a cyclone, a bag filter, or the like. Note that, as a pre-process for these operations, the dispersion may be condensed through a method such as heated spin-drying, separation through filtration, centrifugal separation, decantation, or the like, and, if necessary, the dispersion may be rinsed with water.

As necessary, the oil-including silicone elastomer particles according the present invention may be subjected to a surface treatment, to further improve the effect of preventing agglomeration of the silicone elastomer particles according to the present invention. Moreover, surface treatments may be performed using other known hydrophilic treating agents or hydrophobic treating agents. Arbitrarily, the oil-including silicone elastomer particles produced may have the surfaces thereof, in whole or in part, coated with inorganic microparticles, such as silica, with silicone resin, or the like. Furthermore, if necessary the oil-including silicone elastomer particles may be crushed or pulverized using mechanical forces, and may be graded using a known technique.

[Cosmetic Raw Materials and Cosmetic Compositions]

The silicone elastomer particle according to the present invention is used as a raw material for cosmetics, and when mixed into a cosmetic composition, or the like, has low oil absorption, is superior in improving the effects of softness and the texture and feel in use as a cosmetic, and, when compared to a conventional silicone elastomer particle or oil-including silicone particle, suppresses agglomeration over time, and is remarkably superior in ease of handling, storage stability, and stability when blended as a cosmetic raw material, or the like.

In particular, the oil-including silicone elastomer particles according the present invention, when compared to known oil-including silicone particles, are resistant to agglomeration with the passage of time, and thus even if stored over an extended period of time, there is no need for a stirring or crushing operation prior to mixing, and thus not only is the ease of handling and storage stability superior, but also there is uniform dispersibility into the cosmetics, enabling more uniform mixing with the pigments, and the like, included in the cosmetics, making it possible to improve the appearance and feeling in use of the cosmetics. In addition to this, the oil-including silicon elastomer particles according the present invention have oil absorbing properties not found in conventional silicone elastomer particles, that of low oil absorption, and also enables uniform dispersibility into other cosmetic raw materials that are lipophilic (and particularly into oily raw materials), and thus has benefits such as increasing the flexibility in composition design, and of superior feeling in use through the application of a soft feeling and spreadability through preventing the cosmetic from being oily or tacky where applied to the skin or the hair, as no oily raw material is absorbed with the passage of time, which would lead to thickening or a change in the feel when mixed into the cosmetic product.

Moreover, in the oil-including silicone elastomer particles according the present invention, there is high flexibility in design of the cross-linking structure density and in selecting the oil, where a variety of oils for cosmetic applications can be included in the cross-linking structures based on the cross-linking reaction of higher alkenyl groups, thus making it possible to apply, as desired, a feeling of flexibility to the silicone elastomer particles, to improve the feel that is derived from the oil within the particles, and to improve the cosmetic performance. Moreover, dispersion, into the oil, of functional components, such as lipophilic cosmetic raw materials, medications, or the like, and inclusion thereof in the silicone elastomer particles, makes it possible also to design oil-including silicone elastomer particles that have functions resembling that of drug delivery through gradual release of these components into the skin or the hair.

While there are no particular limitations on the types of cosmetic compositions that include the oil-including silicone elastomer particles according to the present invention, they may be, for example: cosmetics for cleaning, such as soaps, body washes, cleansing creams, and the like; base cosmetics such as skin lotions, creams and milky lotions, packs, and the like; base makeup cosmetics such as face powders, foundations, and the like; facial cosmetics such as lipsticks, blushers, eyeshadows, eyeliners, mascaras, and the like; makeup cosmetics such as nail polishes, and the like; hair cosmetics such as hair rinses, hairstyling agents, hair restoring agents, hair conditioning agents, hair dyes, and the like; fragrant cosmetics such as perfumes, colognes, and the like; toothpastes; bath products; or specialty cosmetics such as depilatory agents, shaving lotions, antiperspirants/deodorizing agents, sun blocks, and the like. Moreover, the forms of these cosmetic compositions may be, for example, aqueous liquids, oily liquids, emulsions, creams, foams, semi-solid shapes, solid shapes, powdery, or the like. Moreover, these cosmetic compositions may be used as sprays.

In these cosmetic compositions, the inclusion proportions of the oil-including silicone elastomer particles described above preferably are in a range of between 0.5 and 99.0 mass % in the cosmetic compositions, and particularly preferably in a range between 1.0 and 95 mass %. This is because if the inclusion proportion of the oil-including silicone elastomer particles were in excess of the upper limit of the range described above, the effect as a cosmetic would be lost, and if less than the lower limit of the range described above, it would have little improvement in the feeling of the cosmetic composition in use.

The oil-including silicone elastomer particles according to the present invention may be used to replace some or all of the silicone-based particles for the silicone particles (silicone rubber powders, or the like) or cosmetic compositions that include silicone compound particles (and, particularly in the examples of preparations) proposed in Patent Document 1 (Japanese Unexamined Patent Application Publication H07-316014), Patent Document 2 (International Patent Application Publication WO 2017/191798), Patent Document 3 (Japanese Unexamined Patent Application Publication H02-243612), Japanese Unexamined Patent Application Publication 2011-105663, Japanese Unexamined Patent Application Publication 2011-168634, and Japanese Unexamined Patent Application Publication 2011-102354, and Japanese Unexamined Patent Application Publication 2014-122316, which may further improve the feeling in use of the cosmetic compositions, and the production efficiency thereof, proposed in these patent documents. Note that, as described above, the examples of cosmetic compositions that include silicone particles (such as silicone rubber powders) or silicone composite particles into which are mixed the oil-including silicone elastomer particles according to the present invention are of course not limited to those that are described above, but rather a preparation may be designed wherein some or all of the silicone particle components within a commercially available cosmetic are replaced by the oil-including silicone elastomer particles according the present invention through a common technique by a person skilled in the art.

Moreover, the oil-including silicone elastomer particles according to the present invention may be applied in replacing some or all of the silicone-based particles in the applications and preparations of cosmetic compositions disclosed in the patent documents described above, and these uses are also included in the scope of the invention in the present application. As one example, the oil-including silicone elastic particles according the present invention may be, and preferably are, combined with arbitrary components such as: cosmetic media (aqueous media or oily media) disclosed in the cosmetic composition, oily media (including oil agents and volatile oil agents), water, coloring agents, pigments, ultraviolet radiation protecting components, alcohols, water-soluble polymers, film-forming agents, oil agents, oil-soluble gelling agents, organically modified clay minerals, surface activating agents, resins, salts, moisture retaining agents, preservatives, antibacterial agents, antioxidants, pH adjusters, chelating agents, cooling agents, anti-inflammatory agents, components for skin beautification (whitening agents, cell activating agents, skin roughening agents, blood circulation promoting agents, skin astringents, antiseborrheic agents, etc.), vitamins, amino acids, nucleic acids, hormones, clathrates and the like, physiologically active substances, pharmaceutically active ingredients, and fragrances, and the like, with methods and quantitative ranges selected in the same manner as disclosed in Patent Document 2 (International Patent Application Publication WO 2017/191798).

In particular, the oil-including silicone elastomer particles according to the present invention, when compared with conventional known silicone particles or silicone composite particles that are coated with silsesquioxane, or known oil-including silicone particles, have superiority in terms of ease of handling, storage stability, and low oil absorption, and, in particular can achieve an ideal appearance, feel in use, and the like, in:

(1) cosmetic compositions and preparations that include oily media (oily cosmetic raw materials), such as oil;

(2) cosmetic compositions and preparations that include lipophilic ultraviolet radiation protection components (such as for example, octylparamethoxycinnamic acid); and (3) cosmetic compositions and preparations that include inorganic powders such as coloring agents, pigments, or the like.

These specific preparations are described in further detail in the embodiments below.

In addition, because, with the oil-including silicone elastomer particles according to the present invention the aqueous dispersion can be designed easily, it is possible to achieve an ideal feeling in use, with superior flexibility in the design of the preparation and superior mixture stability, in aqueous cosmetic compositions and preparations as well. These specific preparations will be described in more detail in the embodiments below.

In manufacturing a cosmetic according to the present invention, the cosmetic raw material according to the present invention, as described above, can be mixed uniformly with other cosmetic raw materials easily, enabling easier manufacturing. The various types of mixing equipment and kneading equipment normally used in manufacturing of cosmetics may be used as the mixing means. The device may be, for example, a homomixer, a paddle mixer, a Henschel mixer, a homo disper, a colloid mixer, a propeller stirring apparatus, a homogenizer, an in-line-type continuous emulsifier, an ultrasonic emulsifier, a vacuum-type frozen mixer, or the like.

[Organic Resin Additives, Organic Resin, Coating, and Coating Agent]

The oil-including silicone elastomer particles according the present invention are extremely useful as an organic resin additive as well, given the characteristics thereof, described above. Specifically, the oil-including silicone elastomer particles according to the present invention are superior in uniformity of dispersion into an organic resin, and, if desired, in terms of stress relaxation characteristics, and the like, and remarkably superior in terms of ease of handling and storage stability due to being resistant to producing agglomeration, even when stored over an extended period of time. Moreover, the member, coating film, or coating wherein the organic resin, into which the oil-including silicone elastomer particles have been mixed, has been cured has softness (including softness of the coating layer), durability, adhesion to the substrate, and improved compliance, and, in particular, has superior softness, heat resistance, and shock resistance, and thus is extremely useful as a highly functional organic resin, coating, or coating agent used in electronic materials.

[Organic Resin]

The organic resin that includes the oil-including silicone elastomer particles according to the present invention preferably is a curable organic resin composition or thermoplastic resin. Of these, the curable resin is suitable as an electronic material such as a semiconductor substrate, or the like. More specifically, the curable organic resin composition may be, for example, a phenol resin, a formaldehyde resin, a xylene resin, a xylene-formaldehyde resin, a ketone-formaldehyde resin, a furon resin, a urea resin, an imide resin, a melamine resin, an alkyd resin, an unsaturated polyester resin, an aniline resin, a sulfone-amide resin, a silicone resin, an epoxy resin, or a copolymerized resin of these resins. These curable resins may be used in combination of two or more of the above. In particular, the cured resin preferably is one or more selections from a group comprising epoxy resins, phenol resins, imide resins, and silicone resins. The epoxy resin should be a compound that includes a glycidyl group or an alicyclic epoxy group and may be, for example, an o-cresol novolac-type epoxy resin, a phenol novolac-type epoxy resin, a biphenyl-type epoxy resin, a bisphenol A-type epoxy resin, a bisphenol F-type epoxy resin, a dicyclopentadiene-type epoxy resin, a naphthalene-type epoxy resin, an anthracene-type epoxy resin, a naphthol aralkyl-type epoxy resin, a polyvinylphenol-type epoxy resin, a diphenylmethane-type epoxy resin, a diphenylsulfone-type epoxy resin, a triphenolalkane-type epoxy resin, a cresol/naphthol co-condensation-type epoxy resin, a bisphenylethylene-type epoxy resin, a fluorene-type epoxy resin, a stilbene-type epoxy resin, a spirocoumarone-type epoxy resin, a norbornene-type epoxy resin, a terpene-type epoxy resin, a phenol cyclohexane-type epoxy resin, a halogenated epoxy resin, an imide group-containing epoxy resin, a maleimide group-containing epoxy resin, an allyl group-modified epoxy resin, a silicone-modified epoxy resin, or the like. Moreover, the phenol resin may be of a polyvinylphenol type, a phenol novolac type, a naphthol type, a terpene type, a phenol dicyclopentadiene type, a phenol aralkyl type, a naphthol aralkyl type, a triphenol alkane type, a dicyclopentadiene type, a cresol/naphthol co-condensation type, a xylene/naphthol co-condensation type, or the like. Furthermore, the silicone resin may be an epoxy-modified silicone resin wherein an epoxy resin has been reacted with the silanol groups or silicon atom-bound alkoxy groups in a silicone resin. The curing mechanism for such a curable resin may be that of a thermally curable type, an energy beam curable type through ultraviolet light, radiation, or the like, a moisture curable type, a condensation reaction curable type, an addition reaction curable type, or the like. Moreover, while there is no particular limitation on the characteristics of such a curable resin at 25° C., preferably it is either a liquid or a solid that is softened through heating.

As other arbitrary components, a curing agent, a curing accelerating agent, a filling agent, a light sensitizing agent, a high-level fatty acid metal salt, an ester-based wax, a plasticizing agent, and the like, can be mixed into the organic resin that includes the oil-including silicone elastomer particles according to the present invention. The curing agent may be: an organic acid such as carboxylic acid, sulfonic acid, or the like, or an anhydride thereof; an organic hydroxy compound; an organic silicon compound that has a silanol group, an alkoxy group, or a halogen group; a primary or secondary amino compound; or the like, and may be a combination of two or more of the above. Moreover, the curing accelerating agent may be: an organic metal compound such as a tertiary amine compound, aluminum, zirconium, or the like; an organic phosphorus compound such as phosphine, or the like; or a heterocyclic amine compound, a boron complex compound, an organic ammonium salt, an organic sulfonium salt, an organic peroxide, or a hydrosilylation catalyst. Additionally, the filling agent may be, for example: a fibrous filling agent such as glass fibers, asbestos, alumina fibers, ceramic fibers that have alumina and silica as components thereof, boron fibers, zirconia fibers, silicon carbide fibers, metal fibers, polyester fibers, aramid fibers, nylon fibers, phenol fibers, natural animal or vegetable fibers, and the like; powderous filling agents such as melted silica, precipitated silica, fumed silica, calcinated silica, zinc oxide, calcinated clay, carbon black, glass beads, alumina, talc, calcium carbonate, clay, aluminum hydroxide, barium sulfate, titanium dioxide, aluminum nitride, silicon carbide, magnesium oxide, beryllium oxide, kaolin, mica, zirconia, and the like; and so forth, where two or more of the above may be combined for use. For an epoxy-based resin, the inclusion of an amine-based curing agent is particularly preferred.

The oil-including silicone elastomer particles according to the present invention may be mixed in as an additive in a thermoplastic resin other than those which are described above, and can be used as an agent for modifying a physical characteristic, such as a surface lubricant, a stress relaxing agent, or the like, or an agent for modifying an optical characteristic, such as a light scattering agent, or the like. There is no particular limitation to the type of thermoplastic resin, which may be at least one polymer selected from a group comprising, for example, polycarbonate-based resins, polyester-based resins, polyether-based resins, polylactic acid-based resins, polyethylenes, polypropylenes, polyolefin-based resins such as ethylene-propylene-based copolymers, or the like, polystyrene-based resins, styrene-based copolymers, fluorine-based polymers such as tetrafluoroethylene, or the like, polyvinyl ethers, and cellulose-based polymers, or a composite resin that combines the above. The silicone resin-coated silicone elastomer particles according the present invention can be dispersed uniformly, using a mixing machine such as a two-axis or one-axis extruder, or a metered mixer, into these thermoplastic resins (including master batches thereof), and can be molded for use into the desired form, such as into the shape of a film.

The amount of the oil-including silicone elastomer particles added can be selected as appropriate depending on the physical properties desired in the organic resin, but generally is in a range of between 0.1 and 30 parts by weight in respect to 100 parts by weight of the organic resin, and should be between 0.5 and 10 parts by weight. This is because if the amount of the particles added were less than the lower limit set forth above, the performance such as in the stress relaxation characteristics in respect to the resin, or the like, may be inadequate, which would reduce the softness, heat resistance, and shock durability of the organic resin cured material produced, and, in particular, because of the tendency for there to be reduced heat resistance and shock durability after absorbing moisture. On the other hand, this is because if greater than the upper limit set forth above, there would not only be a negative effect on the ease of handling given that the organic resin, coating, or coating agent would thicken after mixing, but also because of the tendency toward a negative effect on the mechanical characteristics of the organic resin cured material produced.

If the oil-including silicone elastomer particles according the present invention are mixed into an organic resin, the stress relaxation effects will be superior, enabling mixing into an epoxy resin, or the like, for a printed circuit board to form pre-preg, and, additionally, a copper foil with a resin layer that includes filler particles, for a printed circuit board, equipped with a resin layer that includes the oil-including silicone elastomer particles according to the present invention on one face of a copper foil may be formed, enabling use in a copper clad laminate (CCL) application.

[Coating and Coating Agent]

The coating/coating agent that includes the oil-including silicone elastomer particles according to the present invention may be, for example, of a room temperature curable type, a room temperature drying type, or a heated curable type, and, depending on the characteristics thereof, may be aqueous, oily, or powdery, and further, depending on the resin that is the vehicle, may be, for example, a polyurethane resin coating, a butyral resin coating, a long-oil phthalic acid resin coating, an alkyd resin coating, an amino-alkyd resin coating made from an amino resin and an alkyd resin, an epoxy resin coating, an acrylic resin coating, a phenol resin coating, a silicone-modified epoxy resin coating, a silicone-modified polyester resin coating, a silicone resin coating, or the like.

The amount of oil-including silicone elastomer particles according the present invention that are added may be selected appropriately depending on the physical properties desired in the coating or coating agent, but in order to apply a soft delustered nature uniformly to the coating film that is produced, preferably it is in a range of between 0.1 and 150 parts by weight in respect to 100 parts by weight of the solid content of the coating, and more preferably in a range between 0.1 and 100 parts by weight, and particularly in a range between 0.1 and 50 parts by weight, or between 0.1 and 20 parts by weight. If the amount of particles added were less than the lower limit set forth above, there would be inadequate performance such as the delustering performance in the coating film, adhesion, stress relaxing performance, and the like, and if greater than the upper limits set forth above, the organic resin, coating, or coating agent would thicken after mixing, which would have a negative effect on the ease of handling.

The coating or coating agent that includes the oil-including silicone elastomer particles according to the present invention may include: alcohols such as methanol, ethanol, and the like; ketones such as methyl ethyl ketone, methyl isobutyl ketone, and the like; esters such as ethyl acetate, butyl acetate, cellosolve acetate, and the like; amides such as N,N-dimethyl formamide; olefins such as hexane, heptane, octane, and the like; organic solvents such as aromatic hydrocarbons such as toluene, xylene, and the like; known inorganic filling agents such as reinforced silica, and the like, organic filling agents, curing accelerating agents, silane coupling agents, pigments such as carbon black, dyes, oxidation inhibitors, thickening agents made from polymer compounds, flame retardant agents, and weather durability bestowing agents.

EMBODIMENTS

The oil-including silicone elastomer particles, the manufacturing method thereof, and the cosmetics including the same, according to the present invention, will be explained in greater detail through the embodiments and the reference examples. However, the present invention is not limited to only these embodiments. Viscosities in the embodiments are values at 25° C. Moreover, the characteristics of the individual silicone particles are measured as below. Note that in the embodiments, unless otherwise noted "silicone particle" is a general term for a particle comprising a silicone cured material (a cured silicone particle), and does not include emulsions.

[JIS a Hardness of the Silicone Particles]

(1) An isopropyl alcohol solution of chloroplatinic acid and a curable silicone composition that is the raw material for the silicone particles, in a state that does not include oil, was heated for one hour at 150° C. in an oven, to cure into a sheet. The hardnesses thereof were measured by a JIS A hardness meter specified in JIS K 6253, and defined as the hardnesses of the oil-including silicone particles in a state wherein oil is not included.

(2) An isopropyl alcohol solution of chloroplatinic acid and a mixture of the oil and the curable silicone composition that is the raw material for the oil-including silicone particles was heated for one hour at 150° C. in an oven, to cure into a sheet. The hardnesses thereof were measured by a JIS A hardness meter specified in JIS K 6253, and defined as the hardnesses of the oil-including silicone particles.

[Amount of Residual SiH in the Silicone Particles]

An ethanol solution of potassium hydroxide with a density of 40%, in respect to a unit mass, was added to the cured silicone particles and allowed to rest for one hour, and hydrogen gas produced up until the reaction end point was reached was trapped, and through headspace gas chromatography, the amount of trapped hydrogen produced was measured, to measure the per-unit mass amount of remaining silicon atom-bound hydrogen atoms.

[Average Primary Particle Diameters of the Emulsion Particles]

In regard to the emulsions prior to addition of the platinum catalyst, the cross-linkable silicone emulsion particles were measured through a laser diffraction-type grain size distribution measuring instrument (LS-230, manufactured by Beckman Coulter), and the median diameter (the "50% particle size," which is the particle size corresponding to 50% in the cumulative distribution) was defined as the average particle size and listed in the table as "Emulsion Particle Size μm."

[AVERAGE PARTICLE DIAMETERS OF THE SILICONE PARTICLES (POWDER)]

With ethanol as the dispersing agent, the particle sizes of the cured silicone particles were measured using a laser diffraction-type grain-size distribution measuring instrument (LA-750, by Horiba, Ltd.), to list in the table, as "Cured Particle Diameter μm," the values for the median diameter of the cured silicone particles in the ethanol (D90, in micrometer, which is the particle size corresponding to 50% in the cumulative distribution), and the arithmetic deviation (SD, in μm²), which indicates the variation in the particle size distribution). For the measurement samples, cured silicone particles (1 g) and ethanol (100 mL) were dispersed in a 300 mL cup using a stirring blade and ultrasonic vibration equipment.

[Method for Measuring the Quantity of Oil Absorbed by the Powder]

1 g of cured silicone particles was placed in a 100 mL beaker, and oil (squalane or decamethyl cyclopentasiloxane (D5)) was dripped in, one drop at a time, while stirring the silicone particles slowly with a glass rod, and the volume of oil drips required to form a uniform paste of cured silicone particles and oil was calculated. The proportion of the volume of the oil dripped, in respect to the cured silicone particles, was defined as the quantity of oil absorbed (g).

[Method for Measuring the Amount of Absorption of Artificial Skin Oil]

The amount of absorption of the artificial skin oil (oil mixture), described below, was carried out using the same method as the method for measuring the amount of absorption of oil of the powder, described above.

Triglyceride oleate/oleic acid/squalane were mixed so as to have a mass ratio of 6/2/2 (hereinafter termed simply "artificial skin oil").

[Method for Measuring the Bulk Density of the Silicone Particles]

100 mL of cured silicone particles was placed in a 100 mL cup, cured silicone particles were scraped off the top of the cup, and the weight of the silicone particles, less the weight of the cup, was measured. The weight (g) of the cured silicone particles produced was divided by the volume (mL), to calculate the bulk density of the cured silicone particles.

The average formulas for components of (A) and component (B) used in the reference examples are listed below.

In the formulas below, "Vi" indicates a vinyl group that is expressed as $CH_2=CH-$, "Me" indicates a methyl group that is expressed by $CH_3-$, and "He" indicates a hexenyl group that is expressed by $CH_2=CH-CH_4H_8-$.

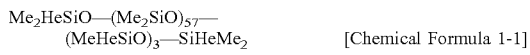 [Chemical Formula 1-1]

Alkenyl group inclusion proportion: 2.7 wt %. Viscosity: 100 mPa·s.

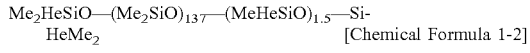 [Chemical Formula 1-2]

Alkenyl group inclusion proportion: 0.97 wt %. Viscosity: 420 mPa·s.

 [Chemical Formula 1-3]

Alkenyl group inclusion proportion: 0.47 wt %. Viscosity: 360 mPa·s.

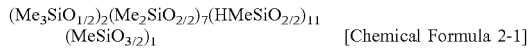 [Chemical Formula 2-1]

Silicon atom-bonded hydrogen atom inclusion proportion: 0.825 wt %. Viscosity: 15 mPa·s.

 [Chemical Formula 2-2]

Silicon atom-bonded hydrogen atom inclusion proportion: 0.043 wt %. Viscosity: 64 mPa·s.

The types of oils used in the oil-including silicone elastomer particles in the embodiments and the reference examples, and the viscosities thereof at 25° C., were as follows. Note that these oils were liquid, with good fluidity, at 40° C.

Oil 1: Both-end trimethylsiloxylated dimethylpolysiloxane
  (Viscosity 100 mPa·s at 25° C.)
Oil 2: Decamethyl cyclopentasiloxane
  (Viscosity 3.8 mPa·s at 25° C.)
Oil 3: Side chain polyether-modified polysiloxane
  (Viscosity 130 mPa·s at 25° C.)
Oil 4: Trimethyl pentaphenyl trisiloxane
  (Viscosity 175 mPa·s at 25° C.)
Oil 5: Higher alkyl-modified polysiloxane with C16-alkyl groups on the side chain
  (Viscosity 45 mPa·s at 25° C.)

Embodiment 1: C6 Silicone Elastomer Particles Including 33% Oil 1

A polyorganosiloxane, expressed by the average formula of [Chemical Formula 1-2], and a polyorganosiloxane expressed by the average formula of [Chemical Formula 2-1] were mixed uniformly at room temperature with a mass ratio of 89:11, after which the oil 1, described above, was added in an amount so as to be 33% of the composition as a whole (that is, so that the oil inclusion proportion in the oil-including silicone elastomer particles after curing would be 33%), and mixed, to produce a cross-linkable composition. Following this, the composition was dispersed into an aqueous solution at 25° C. made from 3.0 parts by weight of polyoxyethylene alkyl (C12-14) ether and 20 parts by weight purified water, and following uniform emulsification using a colloid mill, this was diluted through adding 350 parts by weight purified water, to prepare an emulsion that includes a cross-linkable silicone emulsion particle comprising the cross-linkable silicone composition described above and oil 1. Next an isopropyl alcohol solution of chloroplatinic acid (in an amount such that the platinum metal in the composition will be 10 ppm, in terms of mass) was formed into an aqueous solution, with polyoxyethylene alkyl (C12 through 14) ether and purified water, and added to the emulsion, and after stirring, the emulsion was allowed to rest for three hours at 50° C., to prepare a uniform aqueous suspension of the oil-including silicone elastomer particles. Following this, the aqueous solution was dried using a small spray dryer (manufactured by Ashizawa-Niro), to produce the oil-including silicone elastomer particles. The physical properties, such as the JIS-A hardness, of the oil-including silicone elastomer particles produced are shown in Table 1.

Embodiment 2: C6 Silicone Elastomer Particles Including 40% Oil 1

Aside from adding the oil 1 in an amount so as to be 40% of the composition as a whole (that is, in an amount so that the oil inclusion proportion in the oil-including silicone elastomer particles after curing would be 40%), oil-including silicone elastomer particles were produced in the same manner as in the first embodiment. The physical properties, such as the JIS-A hardness, of the oil-including silicone elastomer particles produced are shown in Table 1.

Embodiment 3: C6 Silicone Elastomer Particles Including 30% Oil 1

A polyorganosiloxane, expressed by the average formula of [Chemical Formula 1-1], and a polyorganosiloxane expressed by the average formula of [Chemical Formula 2-1] were mixed uniformly at room temperature with a mass ratio of 89:11, after which the oil 1, described above, was added in an amount so as to be 33% of the composition as a whole (that is, so that the oil inclusion proportion in the oil-including silicone elastomer particles after curing would be 33%), and mixed, to produce a cross-linkable composition. Following this, the composition was dispersed into an aqueous solution at 25° C. made from 3.0 parts by weight of polyoxyethylene alkyl (C12-14) ether and 20 parts by weight purified water, and following uniform emulsification using a colloid mill, this was diluted through adding 350 parts by weight purified water, to prepare an emulsion that includes a cross-linkable silicone emulsion particle comprising the cross-linkable silicone composition described above and oil 1. Next an isopropyl alcohol solution of chloroplatinic acid (in an amount such that the platinum metal in the composition will be 10 ppm, in terms of mass) was formed into an aqueous solution, with polyoxyethylene alkyl (C12 through 14) ether and purified water, and added to the emulsion, and after stirring, the emulsion was allowed to rest for three hours at 50° C., to prepare a uniform aqueous suspension of the oil-including silicone elastomer particles. Following this, the aqueous solution was dried using a small spray dryer (manufactured by Ashizawa-Niro), to produce the oil-including silicone elastomer particles. The physical properties, such as the JIS-A hardness, of the oil-including silicone elastomer particles produced are shown in Table 1.

Embodiment 4: C6 Silicone Elastomer Particles Including 33% Oil 2

An aqueous suspension of oil-including silicone elastomer particles was produced in the same manner as in Embodiment 1, except for producing a uniform aqueous suspension of oil-including silicone elastomer particles according to each of the embodiments produced through this manufacturing process through adding the same amount of an oil 2, instead of the oil 1, and not removing the water content. The physical properties, such as the JIS-A hardness, of the oil-including silicone elastomer particles produced are shown in Table 1. Note that for this embodiment, the oil absorption was not measured directly.

Embodiment 5: C6 Silicone Elastomer Particles Including 33% Oil 3

An oil-including silicone elastomer particle was produced in the same manner as with Embodiment 1, except for replacing the oil 1 with the same amount of an oil 3. The physical properties, such as the JIS-A hardness, of the oil-including silicone elastomer particles produced are shown in Table 1. Note that because the oil 3 was a polyether modified silicone, the oil-including silicone elastomer particles produced were extremely superior in dispersibility in water.

Embodiment 6: C6 Silicone Elastomer Particles Including 20% Oil 4

Aside from adding an oil 4, instead of the oil 1, in an amount so as to be 20% of the composition as a whole (that is, in an amount so that the oil inclusion proportion in the oil-including silicone elastomer particles after curing would be 20%), oil-including silicone elastomer particles were produced in the same manner as in the first embodiment. The physical properties, such as the JIS-A hardness, of the oil-including silicone elastomer particles produced are shown in Table 1.

Embodiment 7: C6 Silicone Elastomer Particles Including 10% Oil 5

Aside from adding an oil 5, instead of the oil 1, in an amount so as to be 10% of the composition as a whole (that is, in an amount so that the oil inclusion proportion in the oil-including silicone elastomer particles after curing would be 10%), oil-including silicone elastomer particles were produced in the same manner as in the first embodiment. The physical properties, such as the JIS-A hardness, of the oil-including silicone elastomer particles produced are shown in Table 1.

Reference Example 1: Vinyl (C2) Cross-Linked Silicone Particles Including 33% Oil 1

An oil-including silicone elastomer particle was produced in the same manner as with Embodiment 1 except for the use of a vinyl (C2) group-including polyorganosiloxane, expressed by the average formula [Chemical Formula 1-3] instead of the polyorganosiloxane expressed by the average formula of [Chemical Formula 1-1], and a polyorganosiloxane expressed by the average formula of [Chemical Formula 2-2], instead of the polyorganosiloxane expressed by the average formula of [Chemical Formula 2-1], at a mass ratio of 95:5. The physical properties, such as the JIS-A hardness, of the oil-including silicone elastomer particles produced are shown in Table 1.

Reference Example 2: C6 Cross-Linked Silicone Elastomer Particles, not Including Oil Oil-including silicone elastomer particles were produced in the same manner as in Embodiment 1, except that oil 1 was not used. The physical properties, such as the JIS-A hardness, of the oil-including silicone elastomer particles produced are shown in Table 1.

Reference Example 3: C6 Cross-Linked Silicone Elastomer Particles, Not Including Oil Oil-including silicone elastomer particles were produced in the same manner as in Embodiment 1, except that oil 3 was not used. The physical properties, such as the JIS-A hardness, of the oil-including silicone elastomer particles produced are shown in Table 1.

TABLE 1

| | Cross-linked Alkylene | Oil | Oil Amount % | JIS Hardness (No Oil) | JIS Hardness (With Oil) | Emulsion Particle Size μm | Cured Particle Size μm | Powder Oil Absorption Amount *1 g | Powder Oil Absorption Amount *2 g | Population Skin Oil Absorption Amount *3 g | Amount of remaining SiH ppm | Bulk Density g/ml |
|---|---|---|---|---|---|---|---|---|---|---|---|---|
| Embodiment 1 | C6 | 1 | 33 | 20 | 9 | 7.9 | 73.7 | 0.32 | 0.61 | 0.20 | 0.08 | 0.34 |
| Embodiment 2 | | 1 | 40 | 20 | 7 | 7.9 | 61.3 | 0.32 | 0.33 | 0.13 | 0.20 | 0.36 |
| Embodiment 3 | | 1 | 33 | 30 | 15 | 7.5 | 39.8 | 0.20 | 0.28 | 0.12 | 0.90 | 0.41 |
| Embodiment 4 | | 2 | 33 | 20 | 10 | 5.0 | 3.5 | Aqueous suspension, so not measured. | | | | |
| Embodiment 5 | | 3 | 33 | 20 | 6 | 6.4 | 27.5 | 0.04 | 0.09 | 0.05 | — | 0.53 |
| Embodiment 6 | | 4 | 20 | 20 | 11 | 8.7 | 39.2 | 0.25 | 2.40 | 0.13 | — | 0.61 |
| Embodiment 7 | | 5 | 10 | 20 | 1 | 8.6 | 99.9 | 0.31 | 0.39 | 0.24 | — | 0.49 |
| Reference Example 1 | C2 | 1 | 33 | 30 | 15 | 7.4 | 38.1 | 0.86 | 0.89 | 0.56 | 77.7 | 0.22 |
| Reference Example 2 | C6 | 1 | 0 | 20 | — | 8.3 | 92.0 | 0.38 | 3.44 | 0.30 | 0.40 | 0.30 |
| Reference Example 3 | | 1 | 0 | 30 | — | 7.3 | 35.1 | 0.34 | 2.72 | 0.40 | 1.40 | 0.36 |

*1: Amount of squalane absorbed
*2: Amount of decamethyl cyclopentane siloxane (D5) absorbed
*3: Amount of absorption of artificial skin oil (mixture of triglyceride oleate/oleic acid/squalane with a mass ratio of 6/2/2)

As depicted in Table 1, the oil-including silicone elastomer particles according to Embodiments 1 through 3 were confirmed to have low oil absorption, whether for squalane, which is an organic oil, or D5, which is a silicone-based oil. In particular, when compared with Reference Example 1, which is an existing oil-including silicone particle (vinyl cross-linked), the oil-including silicone elastomer particles according to the present embodiment had low oil absorption for both squalane and D5. Moreover, when compared to Reference Example 2 and Reference Example 3, which are silicone particles cross-linked with hexenyl groups (C6), the same as in the embodiments, there was remarkably low oil absorption, particularly for D5, which is a silicone-based oil. Moreover, as seen in the evaluation result using artificial skin oil, the oil-including silicone elastomer particles according to the embodiments, when compared to the reference examples, have low oil absorption. Because of this, there is little effect, when mixing the preparations, on cosmetic amounts, or the like, from organic oils, silicone-based oils, and skin oils, and it can be anticipated that, on the skin, there will be little absorption of skin oil.

<Evaluation of Agglomeration>

Through the same method as for the average particle diameters for the silicone particles (powder), described above, the particle diameters, both initially and after storage at 50° C. (for one month) of the silicone particles produced were measured, and the rate of change thereof was recorded (in the table below).

TABLE 2

Change in Cured Particle Diameters in Embodiments 1 and 3 and in Reference Example 1

| | Initial Cured Particle Diameter (Median Diameter) (μm) | Cured Particle Diameter after Storage for One Month at 50° C. (Median Diameter) (μm) | Rate of Change in the Particle Diameter (%) |
|---|---|---|---|
| Embodiment 1 | 73.7 | 57.4 | −22% |
| Embodiment 3 | 39.8 | 49.7 | +25% |
| Reference Example 1 | 38.1 | 87.3 | +129% |

Although they are oil-including silicone particles using the same oil, in Embodiment 1 and Embodiment 3 there was no large change in the particle diameters (median diameters) after high temperature storage, while, in contrast, in Reference Example 1, which is a cross-linking structure derived from vinyl groups, the particle diameter (median diameter) after high temperature storage was more than twice as large, confirming that there was severe advancement of agglomeration with the passage of time. Given this, the oil-including silicone particles in the present embodiment not only have low oil absorption, but are also able to suppress agglomeration, and thus can be anticipated to have superior storage stability and ease of handling.

In the preparation disclosed in Patent Document 3 (Japanese Unexamined Patent Application Publication H02-243612), described below, oil-including silicone elastomer particles obtained through Embodiment 3, above (inclusion proportion of oil 1: 33%) and silicone particles of Reference Example 1 were used to prepare oily foundations for evaluation. Moreover, as a reference test, a powder/oil blend was prepared through impregnation of the silicone elastomer particles of Reference Example 3 with 33% oil 1, and then subjected to the same evaluation.

Embodiment 8, Reference Example 4, and Reference Examples: Oily Foundations (Method of Preparation)

After mixing Phase B, described in Table 3, below, until uniform using a blender mixer, Phase A, described in Table 3, below, was heated to 70° C. and added, and stirred until uniform. The sample produced was transferred to a container and cooled until room temperature.

(Method of Evaluation)

<Appearance of Sample>

○: Of the 10 panel members, at least seven answered "has a uniform surface."

Δ: Of the 10 panel members, four to six answered "has a uniform surface."

x: Of the 10 panel members, no more than three answered "has a uniform surface."

<Color Nonuniformity>

○: Of the 10 panel members, at least seven answered "color is uniform."

Δ: Of the 10 panel members, four to six answered "color is uniform."

x: Of the 10 panel members, no more than three answered "color is uniform."

<Spreading on Skin>

○: Of the 10 panel members, at least seven answered "spreads well on skin."

Δ: Of the 10 panel members, four to six answered "spreads well on skin."

x: Of the 10 panel members, no more than three answered "spreads well on skin."

TABLE 3

Composition of Oily Foundation

| Ingredient | Brand Name/Supplier | Embodiment 8 | Reference Examples | Reference Example 4 |
|---|---|---|---|---|
| Phase A | | | | |
| Microcrystalline wax | Refined Microcrystalline Wax/Nikko Rica | 4 | 4 | 4 |
| Ozokerite | Ceresin #810/Nikko Rica | 4 | 4 | 4 |
| Lanolin Alcohol → Replacement | Behenyl Alcohol/Nihon Emulsion | 2 | 2 | 2 |
| Liquid Paraffin | Hicall R-230/Kaneda | 3 | 3 | 3 |
| Sorbitan Sesquioleate | EMALEX SPO-150/Nihon Emulsion | 1 | 1 | 1 |
| Decamethyl Cyclopentasiloxane | Toray • Dow Corning/SH245 | 35 | 35 | 35 |
| Isopropyl Myristate | EXCEPAL IPM/Kao | 2 | 2 | 2 |
| Phase B | | | | |
| Pigment-grade Titanium Oxide | SI-Titanium CR-50/Miyoshi Kasei | 15.7 | 15.7 | 15.7 |
| Yellow Iron Oxide | SA Yellow/Miyoshi Kasei | 1.8 | 1.8 | 1.8 |
| Red Iron Oxide | SA-Bengalese cloisonne/Miyoshi Kasei | 0.4 | 0.4 | 0.4 |
| Black Iron Oxide | SA Black/Miyoshi Kasei | 0.9 | 0.9 | 0.9 |
| Kaolin | White Clay/Alban Muller International | 20 | 20 | 20 |
| Talc | JR-46 R/Asada Seifun | 5 | 5 | 5 |

TABLE 3-continued

Composition of Oily Foundation

| Ingredient | Brand Name/Supplier | Embodiment 8 | Reference Examples | Reference Example 4 |
|---|---|---|---|---|
| Oil-including Silicone Elastomer Particle of Embodiment 3 (Including Oil 1 at 33%) | | 6 | | |
| Powder/Oil Blend *1 (Including Oil 1 at 33%) | | | 6 | |
| Silicone Particle of Reference Example 1 (Including Oil 1 at 33%) | | | | 6 |
| Appearance of Sample | | ○ | ○ | x |
| Color Nonuniformity | | ○ | Δ | x |
| Spreading on Skin | | ○ | Δ | x |

*1: In respect to the silicone particles of reference example 3 powder/oil blend wherein oil 1 is added at an amount to be 33 mass % overall As shown in Table 3, for the powder part, when compared in an identical oily foundation, the oil-including silicone elastomer particles of the embodiment were superior in all evaluations in respect to Reference Example 1, which is an existing oil-including silicone particle (vinyl cross-linked). Moreover, for reference, in a powder/oil blend wherein the same amount of oil was added to a silicone elastomer particle, cross-linked by the same hexenyl groups as in the embodiments, the evaluation in terms of appearance was the same, but the color nonuniformity, the quality of the cosmetic spread on the skin, and the feel in use were not on par with those of the embodiments. Given the evaluations set forth above, the oil-including silicone elastomer particle according to the present invention can be used as a cosmetic raw material that provides cosmetics with superior appearance and feel in use, and these characteristics can be anticipated.

Examples of preparations of cosmetics according to the present invention, in which the oil-including silicone particles that are one form of the present invention can be mixed, are presented below. However, the present invention is not limited thereto. Note that, unless otherwise specified, in the preparations below the "oil-including silicone elastomer particles according to the present embodiment" may refer, without any particular limitation, to any of the oil-including silicone elastomers of Embodiments 1 through 3 and 5 through 7, described above, or to mixtures of two or more thereof. Note that the aqueous suspension of Embodiment 4 may be used as-is as an aqueous preparation.

Preparation Example 1: W/O Cream Foundation (Ingredients)

Phase A

| | |
|---|---|
| Cetyl diglycerol tris (trimethylsiloxy) silyl ethyl dimethicone (Note 1) | 5.0 parts by weight |
| 2) Dimethicone (Note 2) | 4.2 parts by weight |
| 3) Ethylhexyl methoxysilicic acid (Note 3) | 3.3 parts by weight |
| 4) Caprylyl methicone (Note 4) | 3.3 parts by weight |
| 5) Isododecane and (dimethicone/bis-isobutyl PPG-20) cross-polymer (Note 5) | 1.5 parts by weight |
| 6) Oil-including silicone elastomer particles according to the present embodiment | 2.0 parts by weight |

Phase B

| | |
|---|---|
| 7) Titanium oxide, talc, methicone (Note 6) | 4.71 parts by weight |
| 8) Mica, aluminum hydroxide (Note 7) | 2.46 parts by weight |
| 9) Yellow iron oxide (Note 8) | 0.66 parts by weight |
| 10) Red iron oxide (Note 9) | 0.16 parts by weight |
| 11) Black iron oxide (Note 10) | 0.006 parts by weight |
| 12) Cetyl diglycerol tris (trimethylsiloxy) silyl ethyl dimethicone (Note 11) | 0.5 parts by weight |
| 13) Caprylyl methicone (Note 12) | 3.7 parts by weight |

Phase C

| | |
|---|---|
| 14) Purified water | 61.5 parts by weight |
| 15) BG | 8.0 parts by weight |
| 16) Sodium chloride | 1.0 parts by weight |

Note 1:
ES-5600 Silicone Glycero Emulsifier, manufactured by Toray Dow Corning Co.
Note 2:
PMX-200 SILICONE FLUID 2CS, manufactured by Toray Dow Corning Co.
Note 3:
Neo Heliopan AV, manufactured by Symrise
Note 4:
FZ-3196, manufactured by Toray Dow Corning Co.
Note 5:
EL-8050 ID Silicone Organic Elastomer Blend, manufactured by Toray Dow Corning Co.
Note 6:
SA Titan CR-50, manufactured by Miyoshi Kasei
Note 7:
SA Exel Mica JP-2, manufactured by Miyoshi Kasei
Note 8:
SA Yellow UXLO, manufactured by Miyoshi Kasei
Note 9:
SA Red, manufactured by Miyoshi Kasei
Note 10:
SA Black, manufactured by Miyoshi Kasei
Note 11:
ES-5600 Silicone Glycero Emulsifier, manufactured by Toray Dow Corning Co.
Note 12:
FZ-3196, manufactured by Toray Dow Corning Co.

The W/O cream foundation of Preparation 1 was prepared using the procedure described below:
 1. Ingredients 1 through 6 were mixed until uniform.
 2. Ingredients 7 through 13 were mixed using a three-roller milling machine.
 3. Ingredients 14 through 16 were mixed.
 4. 1 and 2, above, were mixed.
 5. While agitating 4, above, vigorously, 3 was added to perform emulsification.

Preparation 2: O/W Foundation
(Ingredients)

| Phase A | |
|---|---|
| 1) Oil-including silicone elastomer particles according to the present embodiment | 18 parts by weight |
| 2) Talc (Note 1) | 18 parts by weight |
| Phase B | |
| 3) Purified water | 20 parts by weight |
| 4) Glycerin | 10 parts by weight |
| Phase C | |
| 5) Sodium polyacrylate, methicone (Note 2) | 1 part by weight |
| 6) DMDM hydantoin, propynyl butylcarbamate iodide (Note 3) | A suitable amount |
| 7) Ethylhexyl salicylic acid (Note 4) | 3 parts by weight |
| 8) Ethylhexyl methoxysilicic acid (Note 5) | 3 parts by weight |
| Phase D | |
| 9) Purified water | 21 parts by weight |
| Phase E | |
| 10) Caprylyl methicone (Note 6) | 2 parts by weight |
| 11) Black iron oxide, methicone (Note 7) | 0.05 parts by weight |
| 12) Red iron oxide, methicone (Note 8) | 0.1 parts by weight |
| 13) Yellow iron oxide, methicone (Note 9) | 0.25 parts by weight |
| 14) Titanium oxide, talc, dimethicone (Note 10) | 3.6 parts by weight |

Note 1:
Si talc, manufactured by Miyoshi Kasei
Note 2:
RM 2051 Rheology Modifier, manufactured by Toray Dow Corning Co.
Note 3:
Glydant Plus, manufactured by Lonza
Note 4:
Neo Heliopan OS, manufactured by Symrise
Note 5:
Escalol 557, manufactured by ISP
Note 6:
FZ-3196, manufactured by Toray Dow Corning Co.
Note 7:
SA-black BL-100, manufactured by Miyoshi Kasei
Note 8:
SA-Bengalese cloisonne, manufactured by Miyoshi Kasei
Note 9:
SI-YELLOW-LLXL0, manufactured by Miyoshi Kasei
Note 10:
SI-titanium CR-50, manufactured by Miyoshi Kasei The O/W cream foundation of Preparation 2 was prepared using the procedure described below:
1. Ingredients 1 and 2 were mixed.
2. Ingredients 3 and 4 were mixed.
3. 1 and 2, above, were mixed.
4. Ingredients 5 through 8 were mixed.
5. Ingredient 9 was added to 4, above, and mixed.
6. Ingredients 10 through 14 were mixed until uniform.
7. All ingredients were mixed.

Preparation 3: W/O BB Cream
(Ingredients)

| Phase A | |
|---|---|
| 1) Lauryl PEG-10 Tris (Trimethylsiloxy) silyl ethyl dimethicone (Note 1) | 3 parts by weight |
| 2) Caprylyl methicone (Note 2) | 14 parts by weight |
| 3) Ethylhexyl methoxysilicic acid (Note 3) | 7.5 parts by weight |
| 4) Hexyl diethylaminohydroxybenzoyl benzoate (Note 4) | 1.5 parts by weight |
| 5) Ethylhexyl salicylic acid | 2.5 parts by weight |
| 6) Trimethylsiloxysilicate, polypropylene silsesquioxane (Note 5) | 2 parts by weight |
| 7) Oil-including silicone elastomer particles according to the present embodiment | 4 parts by weight |
| 8) Phenyl trimethicone (Note 6) | 4 parts by weight |
| Phase B | |
| 9) Glycerin | 8 parts by weight |
| 10) Sodium chloride | 0.7 parts by weight |
| 11) Purified water | 40.8 parts by weight |
| Phase C | |
| 12) Titanium oxide | 5.6 parts by weight |
| 13) Yellow iron oxide (Note 7) | 0.25 parts by weight |
| 14) Red iron oxide (Note 8) | 0.1 parts by weight |
| 15) Black iron oxide (Note 9) | 0.05 parts by weight |
| 16) Phenyl trimethicone (Note 10) | 5.2 parts by weight |
| 17) Zinc oxide (Note 11) | 0.8 parts by weight |
| 18) Lauryl PEG-10 Tris (Trimethylsiloxy) silyl ethyl dimethicone | 1 part by weight |

Note 1:
ES-5300 Formulation Aid, manufactured by Toray Dow Corning Co.
Note 2:
FZ-3196, manufactured by Toray Dow Corning Co.
Note 3:
UVINUL MC80N, manufactured by BASF
Note 4:
A Plus Glanular, manufactured by BASF
Note 5:
MQ-1640 Flake Resin, manufactured by Toray Dow Corning Co.
Note 6:
SH556, manufactured by Toray Dow Corning Co.
Note 7:
SA-IOY-8, manufactured by Miyoshi Kasei
Note 8:
SA-IOR-8, manufactured by Miyoshi Kasei
Note 9:
SA-IOB-8, manufactured by Miyoshi Kasei
Note 10:
SH556, manufactured by Toray Dow Corning Co.
Note 11:
FINEX-30S-LPT, manufactured by Sakai Chemical Industry Co.
Note 12:
ES-5300 Formulation Aid, manufactured by Toray Dow Corning Co.

The BB cream of Preparation 3 was prepared using the procedure described below:
1. Ingredients 1 through 8 were mixed.
2. Ingredients 9 through 11 were mixed.
3. Ingredients 12 through 18 were mixed.
4. 1 and 3, above, were mixed.
5. While agitating 1, above, vigorously, 2 was added slowly to perform emulsification.

Preparation 4: Nonaqueous Foundation
(Ingredients)

| Phase A | |
|---|---|
| 1) Titanium oxide, dimethicone (Note 1) | 49.23 parts by weight |
| 2) Yellow iron oxide, methicone (Note 2) | 9.86 parts by weight |
| 3) Red iron oxide, methicone (Note 3) | 1.97 parts by weight |
| 4) Black iron oxide, methicone (Note 4) | 0.55 parts by weight |
| 5) Cetyl diglycerol tris (trimethylsiloxy) silyl ethyl dimethicone (Note 5) | 1.58 parts by weight |
| 6) Caprylyl methicone (Note 6) | 15.8 parts by weight |
| Phase B | |
| 7) Oil-including silicone elastomer particles according to the present embodiment | 2 parts by weight |
| 8) Cyclopentasiloxane (Note 7) | 13 parts by weight |

-continued

| | |
|---|---|
| 9) Isododecane, (acrylate/polytrimethylsiloxyl methacrylate) copolymer (Note 8) | 5 parts by weight |
| 10) Disteardimonium hectorite (Note 9) | 1 part by weight |

Note 1:
SI-titanium CR-50, manufactured by Miyoshi Kasei
Note 2:
SI-YELLOW-LLXLO, manufactured by Miyoshi Kasei
Note 3:
SA-Bengalese cloisonne, manufactured by Miyoshi Kasei
Note 4:
SA-black BL-100, manufactured by Miyoshi Kasei
Note 5:
ES-5600 Silicone Glycero Emulsifier, manufactured by Toray Dow Corning Co.
Note 6:
FZ-3196, manufactured by Toray Dow Corning Co.
Note 7:
SH245, manufactured by Toray Dow Corning Co.
Note 8:
FA 4002 ID Silicone Acrylate, manufactured by Toray Dow Corning Co.
Note 9:
Bentone (R) 38 V CG, manufactured by Elementis The nonaqueous foundation of Preparation 4 was prepared using the procedure described below:

1. Ingredients 1 through 6 were mixed.
2. Ingredients 7 through 10 were mixed.
3. 1 and 2, above, were mixed.

Preparation 5: Compact Foundation
(Ingredients)

| | |
|---|---|
| 1) Talc (Note 1) | 20 parts by weight |
| 2) Mica (Note 2) | 34.6 parts by weight |
| 3) Titanium oxide (Note 3) | 10 parts by weight |
| 4) Red iron oxide (Note 4) | 1 part by weight |
| 5) Yellow iron oxide (Note 5) | 4 parts by weight |
| 6) Black iron oxide (Note 6) | 0.4 parts by weight |
| 7) Mica (Note 7) | 15 parts by weight |
| 8) Polystyrene (Note 8) | 5 parts by weight |
| 9) Squalane | 3 parts by weight |
| 10) Octyldodecyl myristic acid (Note 9) | 1.2 parts by weight |
| 11) Vaseline | 2.5 parts by weight |
| 12) Dimethicone (Note 10) | 3.3 parts by weight |
| 13) Oil-including silicone elastomer particles according to the present embodiment | 5 parts by weight |

Note 1:
Si Talc, manufactured by Miyoshi Kasei
Note 2:
SI-SERICITE FSE, manufactured by Miyoshi Kasei
Note 3:
SI-Titan CR-50, manufactured by Miyoshi Kasei
Note 4:
SA Red, manufactured by Miyoshi Kasei
Note 5:
SA Yellow UXLO, manufactured by Miyoshi Kasei
Note 6:
SA Black, manufactured by Miyoshi Kasei
Note 7:
SA Excel Mica JP-2, manufactured by Miyoshi Kasei
Note 8:
Fine pearl 3000SPQ, manufactured by Sumitomo Chemical
Note 9:
EXCEPARL OD-M, manufactured by Kao
Note 10:
SH200-5000cs, manufactured by Toray Dow Corning Co.

The compact foundation of Preparation 5 was prepared using the procedure described below:

1. All of the above were mixed.

Preparation 6: W/O Skin Cream
(Ingredients)

| Phase A | |
|---|---|
| 1) Lauryl PEG/PPG-18/18 dimethicone (Note 1) | 2 parts by weight |
| 2) Bis (hydroxyethoxypropyl) dimethicone (Note 2) | 2 parts by weight |
| 3) Isopropyl palmitic acid (Note 3) | 1 part by weight |
| 4) Cyclopentasiloxane (Note 4) | 6.5 parts by weight |
| 5) Mineral oil (Note 5) | 10 parts by weight |
| 6) Vaseline | 1.5 parts by weight |
| 7) Oil-including silicone elastomer particles according to the present embodiment | 5 parts by weight |
| Phase B | |
| 8) Glycerin | 5 parts by weight |
| 9) Sodium chloride | 1 part by weight |
| 10) Purified water | 66 parts by weight |

Note 1:
5200 Formulation Aid, manufactured by Toray Dow Corning Co.
Note 2:
5562 Carbinol Fluid, manufactured by Toray Dow Corning Co.
Note 3:
EXCEPAL IPM, manufactured by Kao
Note 4:
SH245, manufactured by Toray Dow Corning Co.
Note 5:
Hicall K-230, manufactured by Kaneda The W/O skin cream of Preparation 6 was prepared using the procedure described below:

1. Ingredients 1 through 7 were mixed.
2. Ingredients 8 through 10 were mixed.
3. While agitating 1, above, vigorously, 2 was added slowly to perform emulsification.

Preparation 7: Sunblock Nonaqueous Lotion
(Ingredients)

| | |
|---|---|
| 1) Zinc oxide (Note 1) | 6 parts by weight |
| 2) Lauryl PEG-10 Tris (Trimethylsiloxy) silyl ethyl dimethicone (Note 2) | 0.5 parts by weight |
| 3) Hexadecane | 3.5 parts by weight |
| 4) Ethylhexyl methoxysilicic acid (Note 3) | 7.5 parts by weight |
| 5) Dimethicone, dimethicone cross-polymer (Note 4) | 24 parts by weight |
| 6) Cyclopentasiloxane (Note 5) | 60.5 parts by weight |
| 7) Oil-including silicone elastomer particles according to the present embodiment | 2 parts by weight |

Note 1:
FINEX-30S-LPT, manufactured by Sakai Chemical Industry Co.
Note 2:
ES-5300 Formulation Aid, manufactured by Toray Dow Corning Co.
Note 3:
UVINUL MC80N, manufactured by BASF
Note 4:
9041 Silicone Elastomer Blend, manufactured by Toray Dow Corning Co.
Note 5:
SH245, manufactured by Toray Dow Corning Co.

The sunblock nonaqueous lotion of Preparation 7 was prepared using the procedure described below:

1. Ingredients 1 through 3 were mixed (using a bead mill, or the like).
2. Ingredients 4 through 7 were added to the ingredients above and agitated until uniform.

Preparation 8: O/W Wrinkle Cream
(Ingredients)

| Phase A | |
|---|---|
| 1) Cyclopentasiloxane (Note 1) | 11 parts by weight |
| 2) Oil-including silicone elastomer particles according to the present embodiment | 10 parts by weight |
| 3) Lauryl PEG/PPG-18/18 dimethicone (Note 2) | 0.5 parts by weight |
| 4) PEG-12 dimethicone (Note 3) | 4 parts by weight |
| Phase B | |
| 5) Purified water | 72.5 parts by weight |
| Phase C | |
| 6) Polyacrylamide, water, (C13, 14) isoparaffin, LAURETH-7 (Note 4) | 2 parts by weight |

Note 1:
SH245, manufactured by Toray Dow Corning Co.
Note 2:
5200 Formulation Aid, manufactured by Toray Dow Corning Co.
Note 3:
OFX-5329, manufactured by Toray Dow Corning Co.
Note 4:
Simulgel 305, manufactured by SEPPIC S.A.

The O/W wrinkle cream of Preparation 8 was prepared using the procedure described below:
1. Ingredients 1 through 4 were mixed until uniform.
2. Ingredients 4 and 5 were mixed until uniform.
3. 1, above, was added to 2, and mixed until uniform.

Preparation 9: Toilet Water
(Ingredients)

| Phase A | |
|---|---|
| 1. Silicone emulsifier premix *1 | 7.0 parts by weight |
| 2. Trilaurez-4 phosphoric acid *2 | 0.05 parts by weight |
| 3. Ethanol | 2.0 parts by weight |
| Phase B | |
| 4. Water | Remainder |
| 5. Butylene glycol (BG) | 3.0 parts by weight |
| 6. Glycerin | 6.0 parts by weight |
| 7. Dipropylene glycol (DPG) | 2.0 parts by weight |
| 8. Disodium hydrogen phosphate | 0.01 parts by weight |
| 9. Sodium dihydrogen phosphate | 0.01 parts by weight |
| 10. Preservatives | Suitable amount |
| 11. Oil-including silicone elastomer particles according to the fifth embodiment | 5.0 parts by weight |

*1: FB-2540 Emulsifier Blend, manufactured by Toray Dow Corning Co.
*2: Hostaphat KL340D, manufactured by Clariant (Method of Preparation)
1. Phase A is mixed.
2. Phase B is mixed.
3. While agitating phase B, phase A is added slowly.

Preparation 10: W/O Sunblock
(Ingredients)

| Phase A | |
|---|---|
| 1. Silicone emulsifier *1 | 1.5 parts by weight |
| 2. Ethylhexyl methoxysilicic acid *2 | 7.5 parts by weight |
| 3. Hexyl diethylaminohydroxybenzoyl benzoate *3 | 2.0 parts by weight |
| 4. Caprylyl methicone *4 | 2.0 parts by weight |
| 5. Isotridecyl isonononate *5 | 3.0 parts by weight |
| 6. Isohexadecane | 8.0 parts by weight |
| 7. Silicone film forming agent *6 | 1.0 parts by weight |
| 8. Disteardimonium hectorite *7 | 1.0 parts by weight |
| Phase B | |
| 9. Fine titanium oxide *8 | 6.0 parts by weight |
| 10. Silicone dispersing agent *9 | 1.5 parts by weight |
| 11. Isohexadecane | 7.5 parts by weight |
| Phase C | |
| 12. Butylene glycol (BG) | 7.0 parts by weight |
| 13. Sodium citrate | 0.2 parts by weight |
| 14. Sodium chloride | 0.5 parts by weight |
| 15. Water | Remainder |
| Phase D | |
| 16. Oil-including silicone elastomer particles according to the present embodiment | 3.0 parts by weight |

*1: ES-5300 Formulation Aid, manufactured by Toray Dow Corning Co.
*3: UVINUL MC80N, manufactured by BASF
*3: UVINUL A Plus, manufactured by BASF
*4: FZ-3196, manufactured by Toray Dow Corning Co.
*5: Emalex INTD-139, manufactured by Nihon Emulsion Co.
*6: FA-4002ID Silicone Acrylate, manufactured by Toray Dow Corning Co.
*7: Benton 38V, manufactured by Elementis
*8: MTY-02, manufactured by TAYCA
*9: ES-5600 Silicone Glycero Emulsifier, manufactured by Toray Dow Corning Co.

(Method of Preparation)
1. Phase A is mixed.
2. Phase B is mixed.
3. Phase C is mixed.
4. Phase A and phase B are mixed.
5. While agitating phases AB, phase C is added slowly.
6. Phase D is added, and agitated until uniform.

Preparation 11: O/W Sunblock
(Ingredients)

| Phase A | |
|---|---|
| 1. Polysorbate 80 *1 | 1.0 parts by weight |
| 2. Mineral oil *2 | 10 parts by weight |
| 2. Triethyl hexanoate | 5.0 parts by weight |
| 3. Hexyl diethylaminohydroxybenzoyl benzoate *3 | 2.5 parts by weight |
| 4. Ethylhexyl methoxysilicic acid *4 | 7.5 parts by weight |
| 5. Caprylyl methicone *5 | 10 parts by weight |
| 6. Oil-including silicone elastomer particles according to the present embodiment | 5.0 parts by weight |
| 7. Titanium oxide dispersion *6 | 10 parts by weight |
| Phase B | |
| 8. Carbomer 2% aqueous solution *7 | 15 parts by weight |
| 9. Water | Remainder |
| 10. Sodium hydroxide 1% aqueous solution | Suitable amount |
| 11. Butylene glycol (BG) | 5.0 parts by weight |
| 12. Glycerin | 2.0 parts by weight |

*1: Leodore TW-0120V, manufactured by Kao
*2: Hicall K-230, manufactured by Kaneda
*3: UVINUL A Plus, manufactured by BASF
*4: UVINUL MC80N, manufactured by BASF
*5: FZ-3196, manufactured by Toray Dow Corning Co.
*6: MTY-02 40 wt %, cyclopentasiloxane 50 wt %, ES-5600 Silicone Glycerol Emulsifier 10 wt %, manufactured by TAYCA
*7: Carbopol 980, manufactured by Lubrizol (Method of Preparation)
Phase A is mixed.
Phase B is mixed.
While agitating phase B, phase A is added slowly.

Preparation 12: Toilet Water Sheet
(Ingredients)

| Phase A | |
|---|---|
| 1. (Acrylate/alkyl acrylate (C10-30)) cross-polymer *1 | 0.1 part by weight |
| 2. Water | Remainder |
| 3. Sodium hydroxide | Suitable amount |
| Phase B | |
| 4. Glycerin | 4.0 parts by weight |
| 5. Oil-including silicone elastomer particles according to the present embodiment | 2.0 parts by weight |
| 6. Aloe vera water | 0.6 parts by weight |
| 7. Panthenol | 0.3 parts by weight |
| 8. Water | 5.0 parts by weight |
| Phase C | |
| 9. Alkyl benzoate (012-15) | 2.7 parts by weight |
| 10. Polysorbate 20 *2 | 0.5 parts by weight |
| 11. Cross-linked silicone gel *3 | 3.5 parts by weight |
| 12. Cyclopentasiloxane *4 | 5.8 parts by weight |
| 13. Preservatives | Suitable amount |
| 14. Fragrance | Suitable amount |

*1: Carbopol ETD2020, manufactured by Lubrizol
*2: Tween20, manufactured by Croda
*3: 9041 Silicone Elastomer Blend, manufactured by Toray Dow Corning Co.
*4: SH245 Oil, manufactured by Toray Dow Corning Co.

(Method of Preparation)
Phase A is mixed.
While agitating phase A, phase B is added.
While agitating phase AB vigorously, phase C is added.
The emulsion described above is impregnated into a nonwoven fabric.

Preparation 13: Cosmetic Foundation
(Ingredients)

| Phase A | |
|---|---|
| 1. Titanium oxide *1 | 3.0 parts by weight |
| 2. Mica | 10 parts by weight |
| 3. Styrene/acrylate copolymer *2 | 3.0 parts by weight |
| 4. Pearl pigment *3 | 2.0 parts by weight |
| 5. Oil-including silicone elastomer particles according to the present embodiment | 25 parts by weight |
| 6. Talc | 25 parts by weight |
| Phase B | |
| 7. Silicone film forming agent *4 | 5.0 parts by weight |
| 8. Ethylhexyl methoxysilicic acid | 5.0 parts by weight |
| 9. Octocrylene | 2.0 parts by weight |
| 10. Dimethicone *5 | 6.0 parts by weight |
| 11. Preservatives | Suitable amount |
| 12. Fragrance | Suitable amount |
| Phase C | |
| 13. Silica silylate *6 | 4.0 parts by weight |
| Phase D | |
| 14. Water | Remainder |
| 15. Propylene glycol | 2.0 parts by weight |
| 16. PEG-32 | 3.0 parts by weight |

*1: SI-Titan CR-50, manufactured by Miyoshi Kasei
*2: SunSpheres ™ Powder, manufactured by Dow Corp.
*3: Timiron Glam Silver, manufactured by Merck
*4: SH200 2cs, manufactured by Toray Dow Corning Co.
*5: FC5002ID Resin Gum, manufactured by Toray Dow Corning Co.
*6: VM-2270 Aerogel Fine Particles, manufactured by Toray Dow Corning Co.

(Method of Preparation)
Phase A is mixed.
Phase B is mixed.
Phase A and phase B are mixed (phase AB).
Phase D is mixed.
Phase C and phase D are mixed (phase CD).
Phase AB and phase CD, above, are mixed.

Preparation 14: Mousse Blush
(Ingredients)

| Phase A | |
|---|---|
| Vaseline | 10 parts by weight |
| Microcrystalline wax | 5.0 parts by weight |
| Silicone wax *1 | 4.0 parts by weight |
| Phenyl trimethicone *2 | 8.0 parts by weight |
| Phase B | |
| Titanium oxide *3 | 3.0 parts by weight |
| Oil-including silicone elastomer particles according to Embodiment 6 | 8.0 parts by weight |
| Silica silylate *4 | 0.5 parts by weight |
| Silicone dispersing agent *5 | 1.0 parts by weight |
| Carmine | 5.5 parts by weight |
| 10. Titanium oxide *6 | 10 parts by weight |
| Phase C | |
| 11. Silicone film forming agent *7 | 10 parts by weight |
| 12. Cross-linked silicone gel *8 | 10 parts by weight |
| Phase D | |
| 13. Caprylyl methicone *9 | 5.0 parts by weight |
| 14. Dimethicone *10 | 10 parts by weight |
| 15. Fragrance | Suitable amount |
| 16. Preservatives | Suitable amount |

*1: 580 Wax, manufactured by Toray Dow Corning Co.
*2: SH556, manufactured by Toray Dow Corning Co.
*2: Eusolex T-S, manufactured by Merck
*4: VM-2270 Aerogel Fine Particles, manufactured by Toray Dow Corning Co.
*5: ES-5300 Formulation Aid, manufactured by Toray Dow Corning Co.
*6: SI-Titan CR-50, manufactured by Miyoshi Kasei
*7: FC5002ID Resin Gum, manufactured by Toray Dow Corning Co.
*8: EL-7040 Hydro Elastomer Blend, manufactured by Toray Dow Corning Co.
*9: FZ-3196, manufactured by Toray Dow Corning Co.
*10: SH200 2cs, manufactured by Toray Dow Corning Co.

(Method of Preparation)
Phase A is heated to 75° C.
Phase B is mixed.
Phase C is mixed.
Phase C is added to phase B, and heated to 75° C. (Phase BC)
While agitating phase BC, phase A is added slowly. (Phase ABC)
Phase D is added to phase ABC (mixture), and agitated until uniform.

Preparation 15: Eyeshadow
(Ingredients)

| Phase A | |
|---|---|
| Oil-including silicone elastomer particles according to Embodiment 6 | 5.0 parts by weight |
| Ba sulfate | 6.0 parts by weight |
| Zinc stearate | 0.2 parts by weight |
| Talc | 62.6 parts by weight |
| Basic magnesium carbonate *1 | 1.2 parts by weight |
| Titanium oxide *2 | 1.8 parts by weight |
| Preservatives | Suitable amount |
| Phase B | |
| Red no. 7 | 15 parts by weight |

-continued

| Phase C | |
|---|---|
| Octyldodecyl myristate | 2.0 parts by weight |
| Triisostearate PEG-6 *2 | 1.0 parts by weight |
| Stearic acid | 2.0 parts by weight |
| Cross-linked silicone gel *3 | 1.5 parts by weight |
| Silicone film forming agent *4 | 1.5 parts by weight |

*1: Basic magnesium carbonate, manufactured by Merck
*2: SI-Titan CR-50, manufactured by Miyoshi Kasei
*3: 9041 Silicone Elastomer Blend, manufactured by Toray Dow Corning Co.
*4: FC5002ID Resin Gum, manufactured by Toray Dow Corning Co.

(Method of Preparation)
Phase A is mixed.
Phase B is added to phase A and agitated. (Phase AB)
Phase C is heated to 75° C., added to phase AB, and agitated until uniform.
Transferred to a container and compressed.

[Aqueous Suspension of Oil-Including Silicone Elastomer]

In Preparation 16 through Preparation 18, below, rather than removing the water content in the Embodiments 1 through 7, described above, the uniform aqueous suspensions of the oil-including silicone elastomer particles according to each of the embodiments, obtained in the manufacturing processes thereof, are used as-is as cosmetic raw materials.

Preparation 16: O/W Foundation Cream
(Ingredients)

| Phase A | |
|---|---|
| Silicone emulsifier premix *1 | 3.0 parts by weight |
| Cross-linked silicone gel *2 | 25 parts by weight |
| Dimethicone *3 | 2.0 parts by weight |
| Phenyl trimethicone *4 | 2.0 parts by weight |
| Tris (caprylic/capric acid) glyceryl | 3.0 parts by weight |
| Squalane | 5.0 parts by weight |
| Jojoba oil | 3.0 parts by weight |
| Pearl pigment *5 | 2.0 parts by weight |
| Phase B | |
| Water | Remainder |
| 10. Glycerin | 5.0 parts by weight |
| 11. Preservatives | Suitable amount |
| 12. Aqueous suspension of oil-including silicone elastomer according to the present embodiment | 5.0 parts by weight |
| 13. Sodium hyaluronate 1% aqueous solution | 10 parts by weight |

*1: RM 2051 Thickening Agent, manufactured by Toray Dow Corning Co.
*2: 9041 Silicone Elastomer Blend, manufactured by Toray Dow Corning Co.
*3: SH200C 6cs, manufactured by Toray Dow Corning Co.
*4: SH556, manufactured by Toray Dow Corning Co.
*5: TIMIRON SPLENDID RED, manufactured by Merck (Method of Preparation)
Phase A is mixed.
Phase B is mixed.
While agitating phase A, phase B is added slowly.

Preparation 17: O/W Skin Cream
(Ingredients)

| Phase A | |
|---|---|
| 1. Stearic acid | 1.0 parts by weight |
| 2. Polysorbate 80 | 1.2 parts by weight |
| 3. Sorbitan sesquioleate | 0.5 parts by weight |
| 4. Glycerin stearate | 1.5 parts by weight |
| 5. Cetearyl alcohol | 1.5 parts by weight |
| 6. Dimethicone *1 | 5.0 parts by weight |
| 7. Squalane | 5.0 parts by weight |
| 8. Isotridecyl isonononate | 5.0 parts by weight |
| 9. Tris (caprylic/capric acid) glyceryl | 5.0 parts by weight |
| Phase B | |
| 10. Water | Remainder |
| 11. Butylene glycol (BG) | 8.0 parts by weight |
| 12. Sodium hydroxide | Suitable amount |
| Phase C | |
| 13. Carbomer *2 | 0.12 parts by weight |
| 14. Water | 10 parts by weight |
| Phase D | |
| 15. Aqueous suspension of oil-including silicone elastomer according to the present embodiment | 7.0 parts by weight |

*1: SH2000 6cs, manufactured by Toray Dow Corning Co.
*2: Carbopol 980, manufactured by Lubrizol (Method of Preparation)
Phase A is heated to 70° C.
Phase B is heated to 70° C.
While agitating phase A, phase B is added slowly. (Phase AB)
Phase C and phase D are added to phase A, agitated until uniform, and then cooled to room temperature.

Preparation 18: O/W All-in-One Gel
(Ingredients)

| Phase A | |
|---|---|
| 1. Silicone emulsifier *1 | 0.5 parts by weight |
| 2. Dimethicone *2 | 1.0 part by weight |
| 3. Jojoba oil | 1.0 part by weight |
| 4. Cyclopentasiloxane *3 | 2.0 parts by weight |
| Phase B | |
| 5. Water | Remainder |
| 6. Glycerin | 10 parts by weight |
| 7. (Acrylate/alkyl acrylate (C10-30)) cross-polymer*4 | 0.2 parts by weight |
| 8. Triethanol amine (TEA) | Suitable amount |
| 9. Preservatives | Suitable amount |
| 10. Aqueous suspension of oil-including silicone elastomer according to the present embodiment | 5.0 parts by weight |

*1: ES-5373 Formulation Aid, manufactured by Toray Dow Corning Co.
*2: SH200C 6cs, manufactured by Toray Dow Corning Co.
*3: SH245 Oil, manufactured by Toray Dow Corning Co.
*4: Carbopol Ultez20 Polymer, manufactured by Lubrizol (Method of Preparation)
Phase A is mixed.
Phase B is mixed.
While agitating phase B, phase A is added slowly.

Preparation 19: Lip Stain
(Ingredients)

| Phase A | |
|---|---|
| Silica silylate *1 | 1.5 parts by weight |
| Hydrogenated polyisobutene *2 | 10 parts by weight |
| Phase B | |
| Silicone resin wax *3 | 3.0 parts by weight |
| Beeswax | 4.5 parts by weight |
| Preservatives | Suitable amount |

-continued

| Phase C | |
|---|---|
| Titanium oxide *4 | 7.7 parts by weight |
| Red No. 201 lake *5 | 2.75 parts by weight |
| Red no. 202 *6 | 2.75 parts by weight |
| Phase D | |
| Caprylyl methicone *7 | 10 parts by weight |
| Silicone dispersing agent *8 | 2.0 parts by weight |
| Phase E | |
| 11. Barium sulfate | 0.2 parts by weight |
| 12. Oil-including silicone elastomer particles according to the present embodiment | 2.0 parts by weight |
| Phase F | |
| 13. Clay minerals *9 | 7.0 parts by weight |
| 14. Antioxidants | Suitable amount |
| 15. Isododecane | 15 parts by weight |
| 16. Dimethicone *10 | 10 parts by weight |
| 17. Silicone film forming agent *11 | 20 parts by weight |
| 18. Ethylene/octene copolymer. *12 | 0.5 parts by weight |
| 19. Fragrance | Suitable amount |

*1: VM-2270 Aerogel Fine Particles, manufactured by Toray Dow Corning Co.
*2: Pearleme 4, manufactured by NOF Corp.
*3: SW-8005 C30 Resin Wax, manufactured by Toray Dow Corning Co.
*4: Unipure White LC 987 AS-EM, manufactured by Sensient
*5: Unipure Red LC 304, manufactured by Sensient
*6: Unipure Red LC 3079, manufactured by Sensient
*7: SS-3408, manufactured by Toray Dow Corning Co.
*8: ES-5300 Formulation Aid, manufactured by Toray Dow Corning Co.
*9: Bentone Gel (R) ISDV, manufactured by Elementis
*10: SH200 1.5cs, manufactured by Toray Dow Corning Co.
*11: 749 Fluid, manufactured by Toray Dow Corning Co.
*12: EcoSmooth ™ Delight H, manufactured by Dow Chemical (Method of Preparation)

Phase A is mixed.

After melting phase B through heating to 80° C. and then cooling to 60° C., phase A is added and agitated. (Phase AB)

Phase C is agitated until uniform.

Phase C and phase D are mixed. (Phase CD)

Phase CD is added to phase AB, above, and agitated at 60° C. (Phase ABCD)

Phase E is added to phase ABCD, above, and agitated. (Phase ABODE)

Phase F is added to phase ABCDE, above, agitated, and cooled to no higher than 40° C.

Preparation 20: Face Powder (Ingredients)

| Phase A | |
|---|---|
| Talc *1 | 75 parts by weight |
| Sericite *2 | 10 parts by weight |
| Zinc oxide *3 | 5.0 parts by weight |
| Magnesium stearate | 4.0 parts by weight |
| Oil-including silicone elastomer particles according to the present embodiment | 5.0 parts by weight |
| Phase B | |
| 6. Squalane | 1.0 part by weight |

*1: SI-talc, manufactured by Miyoshi Kasei
*2: SI-sericite FSE, manufactured by Miyoshi Kasei
*3: FINEX-30-OTS, manufactured by Sakai Chemical Industry Co.

(Method of Preparation)

Phase A is mixed.

Phase B is added to phase A, and agitated until uniform.

Preparation 21: Hair Chalk (Ingredients)

| Phase A | |
|---|---|
| Talc | 63.7 parts by weight |
| Magnesium stearate | 3.0 parts by weight |
| Methyl paraben | 0.2 parts by weight |
| Propyl paraben | 0.1 parts by weight |
| Oil-including silicone elastomer particles accordingt o the present embodiment | 5.0 parts by weight |
| Titanium oxide *1 | 5.0 parts by weight |
| Phase B | |
| 7. Red No. 202 *2 | 15 parts by weight |
| Phase C | |
| Cross-linked silicone gel *3 | 8.0 parts by weight |

*1: Unipure White LC 987 AS-EM, manufactured by Sensient
*2: Unipure Red LC 3079, manufactured by Sensient
*3: 9041 Silicone Elastomer Blend, manufactured by Toray Dow Corning Co.

(Method of Preparation)

Phase A is mixed.

Phase B is added and mixed.

Phase C is added and mixed.

Transferred to a container and compressed.

[Potential for Use in Industry]

When compared to the known silicone particles or oil-including silicone particles, the oil-including silicone particles according to the present invention have low oil absorption, and suppress agglomeration with the passage of time, and thus have superior storage stability, ease of handling, and mixture stability, and can be mixed easily as additives, and when mixed into cosmetics as cosmetic raw materials, can improve the feel, and thus can be used in skin cosmetics, makeup, and the like. Moreover, taking advantage of the physical properties thereof, the oil-including silicone elastomer particles according the present invention can be used also as an additive for thermally curable resin compositions, thermoplastic resin compositions, and the like, as an application for electronic materials, or as a surface lubricant for plastic films.

The invention claimed is:

1. An oil-including silicone elastomer particle, which is produced by:
  subjecting a cross-linkable silicone emulsion particle to a cross-linking reaction in water;
  wherein the cross-linkable silicone emulsion particle is obtained by:
    emulsifying in water a mixture of:
    (A) a cross-linkable silicone composition comprising at least (a) an organopolysiloxane having at least two alkenyl groups, with carbon numbers between 4 and 20, within the molecule; and
    (B) an oil that is liquid at 40° C.;
  thereby, wherein:
    the silicone elastomer particle includes, within the silicone elastomer particle, the oil that is a liquid at 40° C. (B);
    the silicone elastomer particle has a structure wherein at least two silicon atoms within the silicone elastomer particle are cross-linked through a silalkylene group with a carbon number between 4 and 20; and
    the content of the oil that is a liquid at 40° C. (B) and included in the silicone elastomer particle is in a range of between 5 and 60 mass % with respect to the silicone elastomer particle as a whole.

2. The oil-including silicone elastomer particle as set forth in claim 1, wherein:
   i) the oil-including silicone elastomer particle has a polymer matrix formed by the cross-linking reaction in the presence of water and the oil that is liquid at 40° C. (B); and
   ii) the oil that is liquid at 40° C. (B) is filled densely within the polymer matrix, such that the oil-including silicone elastomer particle subsequently has a lower oil absorption property relative to such oil absorption property of the silicone elastomer particle in a state that was not formed in the presence of the oil that is liquid at 40° C. (B).

3. The oil-including silicone elastomer particle as set forth in claim 1, wherein the oil that is liquid at 40° C. (B) is a non-reactive oil that does not have a reactive functional group within the molecule.

4. The oil-including silicone elastomer particle as set forth in claim 1, wherein the oil that is liquid at 40° C. (B) is selected from the group consisting of silicone oils, hydrocarbon oils, ester oils, and combinations thereof, and that have no reactive functional groups within the molecules.

5. The oil-including silicone elastomer particle as set forth in claim 1, wherein the content of the oil that is a liquid at 40° C. (B) is in a range of between 5 and 50 mass % with respect to the silicone elastomer particle as a whole.

6. The oil-including silicone elastomer particle as set forth in claim 1, wherein the average particle diameter measured through a laser diffraction/scattering method is between 0.5 and 20 μm.

7. The oil-including silicone elastomer particle as set forth in claim 1, wherein for the silicone elastomer particle in a state that does not include oil that is liquid at 40° C., the JIS-A hardness, measured through curing in the form of a sheet, in a state that does not include oil that is liquid at 40° C., of the cross-linkable silicone composition (A) that is used to form the silicone elastomer particle, is in a range between 10 and 80.

8. The oil-including silicone elastomer particle as set forth in claim 1, wherein the silalkylene groups included in the silicone elastomer particles are substantially only silalkylene groups with carbon numbers of between 4 and 8, and wherein the content of the silalkylene groups with carbon numbers of 3 and below is less than 5 mass % with respect to the silicone elastomer particle as a whole.

9. The oil-including silicone elastomer particle as set forth in claim 1, wherein the content of silicon atom-bound hydrogen is no greater than 300 ppm, per unit mass.

10. The oil-including silicone elastomer particle as set forth in claim 1, wherein the cross-linkable silicone composition (A) comprises:
   (a) the organopolysiloxane having at least two alkenyl groups, with a carbon number between 4 and 20, per molecule;
   (b) an organohydrogen polysiloxane having at least two silicon atom-bound hydrogen atoms per molecule; and arbitrarily
   (c) a hydrosilylation reaction catalyst;
   wherein the mole ratio of the alkenyl group content (Alk) of component (a) and the silicon atom-bound hydrogen atom content (H) of component (b) is in a range (H/Alk) of from 0.7 through 1.2.

11. A cosmetic raw material that includes the oil-including silicone elastomer particle as set forth in claim 1.

12. A cosmetic composition that includes the oil-including silicone elastomer particle as set forth in claim 1.

13. An organic resin additive that includes the oil-including silicone elastomer particle as set forth in claim 1.

14. An organic resin that includes the oil-including silicone elastomer particle as set forth in claim 1.

15. The oil-including silicone elastomer particle as set forth in claim 1, having a shape that is spheroidal, spherical, elliptical, or irregular.

16. The oil-including silicone elastomer particle as set forth in claim 15, having a shape that is spheroidal or spherical.

17. The oil-including silicone elastomer particle as set forth in claim 1, wherein:
   the content of the oil that is a liquid at 40° C. (B) is in a range of between 5 and 50 mass % with respect to the silicone elastomer particle as a whole; and
   the oil that is liquid at 40° C. (B) is a non-reactive oil that does not have a reactive functional group within the molecule.

18. The oil-including silicone elastomer particle as set forth in claim 10, wherein subjecting the cross-linkable silicone emulsion particle to a cross-linking reaction in water comprises steps (I) and (II):
   (I) emulsifying, in water, the mixture that comprises;
      the cross linkable composition (A), and
      the oil that is liquid at 40°° C. (B), thereby forming the cross-linkable silicone emulsion particle; and
   (II) curing the cross-linkable silicone emulsion particle produced in step (I), in the presence of water, the hydrosilylation reaction catalyst (c), and the oil that is liquid at 40° C. (B), thereby producing the oil-including silicone elastomer particle.

19. The oil-including silicone elastomer particle as set forth in claim 1, wherein silalkylene groups with carbon numbers of 3 and below are not included within the oil-including silicone elastomer particle.

20. A method for manufacturing the oil-including silicone elastomer particle as set forth in claim 1, the method including steps (I) and (II):
   (I) forming a cross-linkable silicone emulsion particle through emulsifying, in water, a mixture that comprises:
      (A) a cross-linkable silicone composition that comprises:
         (a) an organopolysiloxane having at least two alkenyl groups, with a carbon number between 4 and 20, per molecule;
         (b) an organohydrogen polysiloxane having at least two silicon atom-bound hydrogen atoms per molecule; and arbitrarily
         (c) a hydrosilylation reaction catalyst;
         wherein the mole ratio of the alkenyl group content (Alk) of component (a) and the silicon atom-bound hydrogen atom content (H) of component (b) is in a range (H/Alk) of from 0.7 through 1.2; and
      (B) an oil is liquid at 40° C.; and
   (II) producing the oil-including silicone elastomer particle through curing, in the presence of the (c) hydrosilylation reaction catalyst, the cross-linkable silicone emulsion particle that was produced in step (I).

* * * * *